United States Patent [19]

Haynes et al.

[11] 4,110,604
[45] Aug. 29, 1978

[54] PARTICLE DENSITY MEASURING SYSTEM

[75] Inventors: John L. Haynes, Redwood City; Bernard A. Shoor, Atherton, both of Calif.

[73] Assignee: Becton, Dickinson and Company, Rutherford, N.J.

[21] Appl. No.: 832,893

[22] Filed: Sep. 13, 1977

Related U.S. Application Data

[63] Continuation-in-part of Ser. No. 738,896, Nov. 4, 1976, abandoned.

[51] Int. Cl.² ............................................. G06M 11/00
[52] U.S. Cl. ........................ 235/92 PC; 235/92 CC; 235/92 R; 324/71 CP
[58] Field of Search ......... 235/92 PC, 92 PE, 92 CC, 235/92 PL; 324/71 CP; 364/555

[56] References Cited

U.S. PATENT DOCUMENTS

| | | | |
|---|---|---|---|
| 2,952,777 | 9/1960 | Barnothy | 235/92 PC |
| 3,699,319 | 10/1972 | Berg | 364/555 |
| 3,757,213 | 9/1973 | Coulter et al. | 324/71 CP |
| 3,836,850 | 9/1974 | Coulter | 324/71 CP |
| 3,887,868 | 6/1975 | Guggenbuhl | 324/71 CP |
| 3,982,183 | 9/1976 | Collineau | 235/92 PC |

Primary Examiner—Joseph M. Thesz
Attorney, Agent, or Firm—Flehr, Hohbach, Test, Albritton & Herbert

[57] ABSTRACT

A method and apparatus are provided for determining the count per unit volume, that is, the density of particles such as platelets in diluted whole blood. The invention involves use of known information, namely, the count per unit volume of other (reference) particles, such as red blood cells, also suspended in the same sample of liquid. The other particles are generally distinguishable from the particles of unknown count per unit volume by a difference in some measurable characteristic of the particles, such as size. One embodiment of the invention is characterized by generating electrical pulses which represent detected particles in a sample of liquid of undetermined volume; discriminating between pulses which have different characteristics; separately counting such pulses until the count of particles of known density reaches a corresponding preset number or until a predetermined period of time has elapsed, or until the entire sample of liquid under test has been tested; and displaying the total count of particles of previously unknown density. This total count either corresponds directly to the density of such particles or is an easily converted indication of such particle density.

25 Claims, 11 Drawing Figures

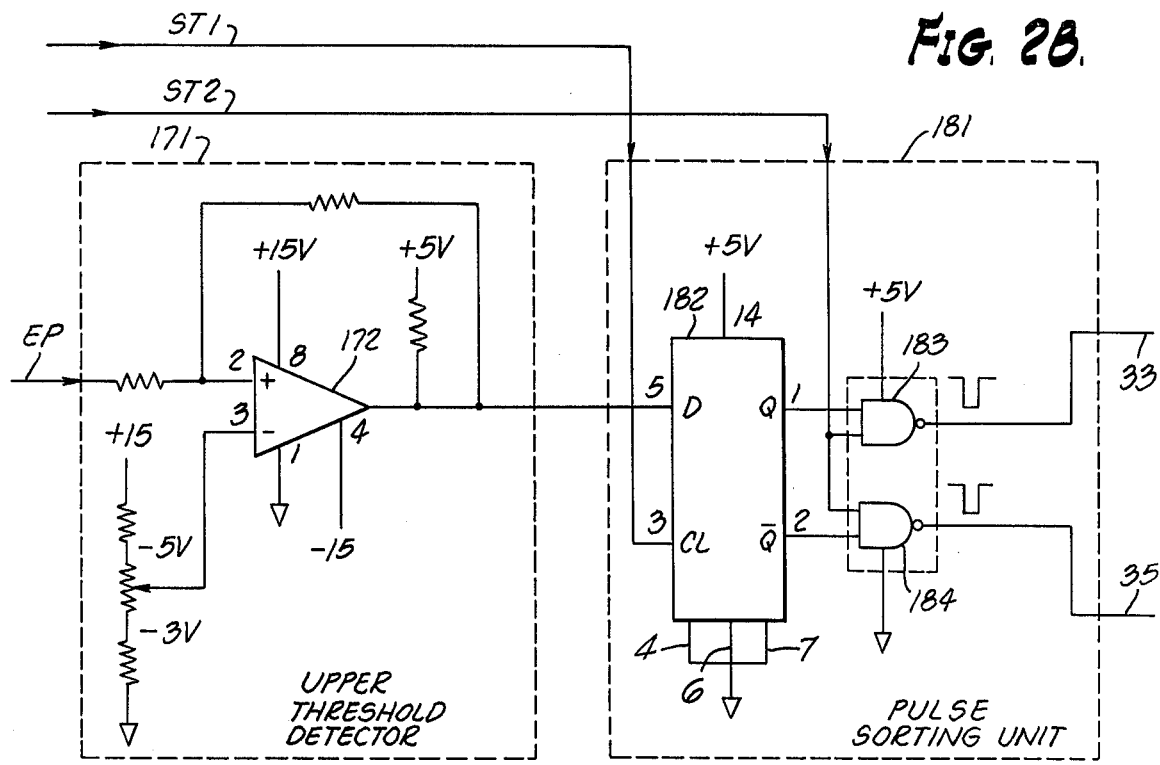

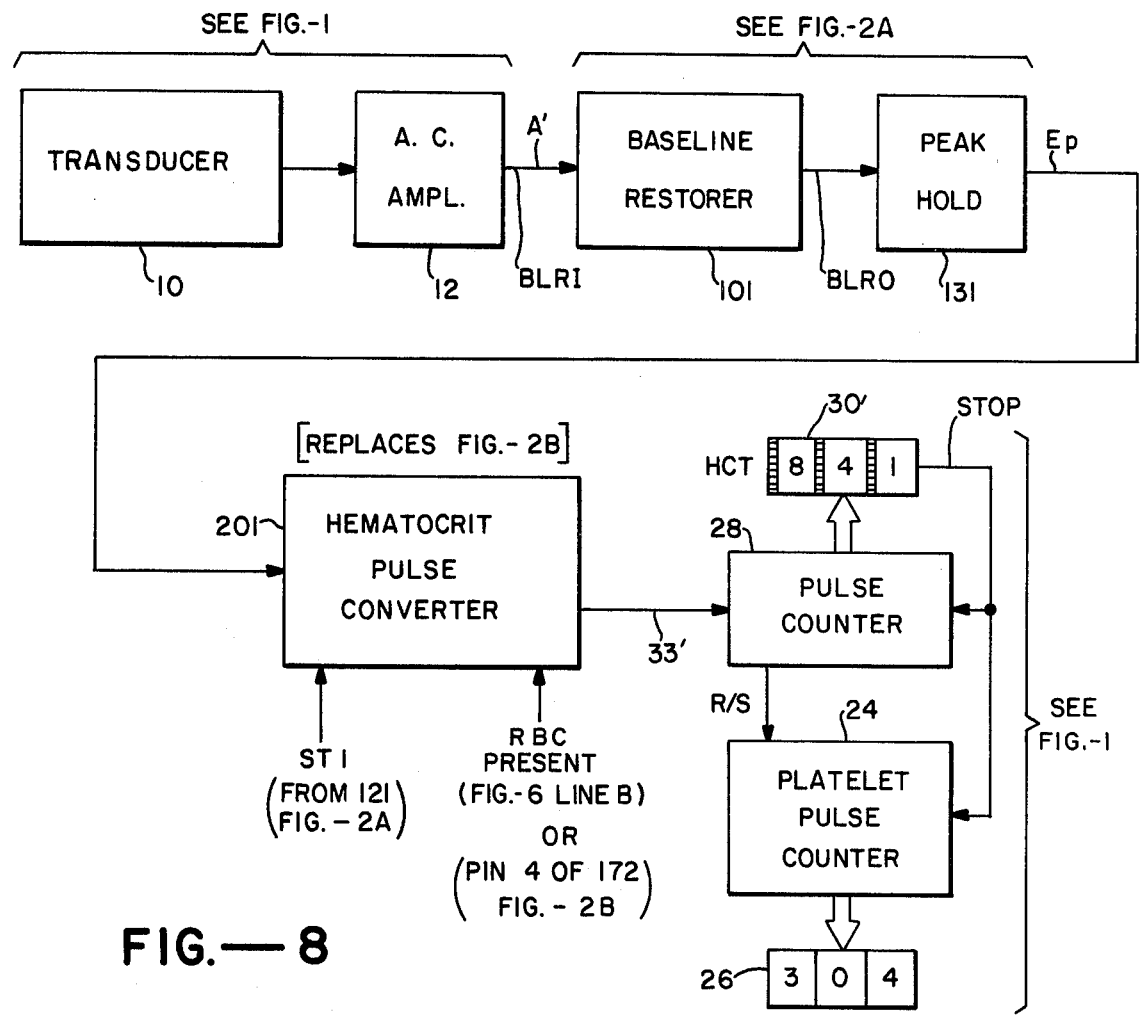
FIG.—8
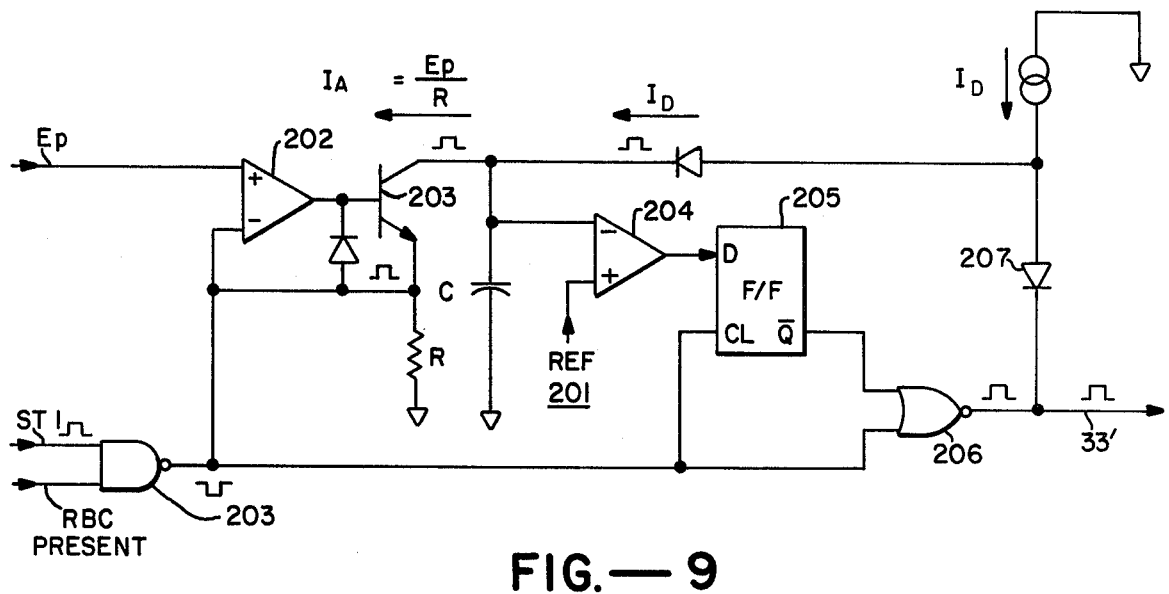
FIG.—9

PARTICLE DENSITY MEASURING SYSTEM

This application is a continuation-in-part of Ser. No. 738,896, filed Nov. 4, 1976, now abandoned.

BACKGROUND OF THE INVENTION

This invention relates to a method and apparatus for determining the density of particles suspended in a fluid. More specifically, this invention relates to a method and apparatus for determining the particle density of a first type of particle suspended in a fluid having at least two types of particles suspended therein where the density of one is easily ascertained or is of standard value. The invention is particularly appropriate for determining a number corresponding to the count of platelets per unit volume of whole blood. Such number is often referred to as the density or concentration of platelets. The density or concentration may also be expressed in terms of particles per unit volume or in terms of hematocrit, that is fractional volume.

The examination of blood is one of the most common and most frequently used methods of medical diagnosis. Normal standard count values of red blood cells, white blood cells, platelets, and other constituent particles of blood and statistical distributions of such count values among healthy individuals have been established. These count values are commonly expressed as count per unit volume or density. Deviations from these standard values are often indicative of the presence of infectious diseases or other medical problems.

The platelet count per unit volume provides an important tool of clinical diagnosis in the examination of blood. Substantial deviation in the count per unit volume of platelets in the blood from a normal value is often indicative of the presence of disease. For example, tuberculosis often causes an increase in the platelet count, while other acute infectious diseases sometimes result in a sub-normal count. A greatly reduced platelet count is often indicative of acute leukemia. Mild drops in the platelet count may also be indicative of adverse drug effects.

Platelets are smaller, and exhibit a lower count, than red blood cells. Typically, normal human blood contains about five million red blood cells per microliter of whole blood and only about two hundred and fifty thousand platelets per microliter. The red blood cell is usually a biconcave disk of about eight microns in diameter and the platelet is a round, oval, or rod shaped particle having a diameter of about two and a half microns.

Because of their smaller size and fewer number compared to red blood cells, platelets are difficult to count in the presence of red blood cells. However, it is desirable to count platelets in the presence of red blood cells because special processes to divide out the platelets or to destroy the red blood cells prior to making a count of platelets, add delay and cost to the process and also reduce the reliability of the process.

In a traditional indirect method of ascertaining the density of platelets, platelets and red blood cells deposited on a microscope slide are counted simultaneously in a selected area, until some minimum number of red blood cells has been counted. The number of platelets is then obtained from the ratio of platelets to red blood cells and the more easily measured red cell density ascertained from a count obtained from a known volume of the same sample of blood.

In one such process, one part of whole blood is usually diluted in 99 parts of a physiological saline solution, such as ISOTON, a product of the Coulter Electronics Company. The mixture is then transferred to a slide and after 15 to 45 minutes, the slide is examined under a microscope. Sometimes the counting is accomplished with the aid of a counting chamber having a plurality of blocks of small squares. The number of particles counted in say ten such blocks is then multiplied by some constant dependent on the dilution ratio and block size. The platelets are visually counted simultaneously with red blood cells until 1,000 red cells have been counted in a common area of the slide. The number of platelets counted is, say, 68. The red cell count per unit volume, that is, the red cell density, will already be known or will become known as a result of other commonly required tests of the blood. For purpose of illustration, we will assume that the red cell density is 4,480,000 per microliter. This represents the actual density measured in a sample to which the invention has been applied.

The platelet density $P_D$ equals the red blood cell density $RBC_D$ multiplied by the ratio of platelets counted to red blood cells counted. In this example:

$$P_D = RBC_D \times (68/1000) = 4,480,000 \times 0.068 =$$
$$304,640 \text{ platelets per microliter.}$$

This method offers the advantage of making the counting process independent of the sample volume as long as the volume of the available sample is large enough to provide a substantial number of platelets (preferably at least 50) and therefore a fairly accurate indication of platelet density. This method and other methods for counting platelets are described by pages 157 to 161 of Todd-Sanford Clinical Diagnosis by Laboratory Methods, Fourteenth Edition, edited by Israel Davidsohn and John Bernard Henry and published by W. B. Saunders Company, 1969.

Such a traditional indirect method of counting platelets and red blood cells simultaneously was either very time consuming or relatively inaccurate due to the paucity of the particles counted. For example in the above illustration, an error in the platelet count of only one platelet would result in a 1.5% error in the platelet density figure. Furthermore, the traditional method of calculating platelet density on the basis of a simultaneous count of red blood cells and platelets, required algebraic manipulation subsequent to completion of the counting process.

Electronic cell counters have made it possible to count particles in the blood in much shorter times with far greater accuracy than was ever possible using traditional microscope techniques.

The general concept of electronically counting different types of particles having distinguishing physical characteristics and suspended in a liquid sample, a known volume of which is passed through a sensing transducer, is old in the art. See for example, Coulter U.S. Pat. No. 2,656,508.

However, so far as is known, electronic particle counting has not been applied heretofore to the traditional indirect method of simultaneously counting red blood cells and platelets to determine the platelet count density of an undetermined volume of diluted whole blood. Furthermore, so far as is known, prior to the invention herein disclosed, there has been no known way of avoiding the algebraic manipulation required subsequent to the simultaneous count of red blood cells and platelets of a blood sample to calculate the platelet count per unit volume.

Though he concentration or density of particles in a fluid mediumis commonly expressed in terms of count per unit volume, it is also sometimes expressed in other ways, such as percent volume. More particularly, in the analysis of blood, routine measurements are often made of both red blood cell count and the hematocrit of the sample, that is its percent of blood volume occupied by red blood cells.

Precise reference values of hematocrit are usually made by a well-known centrifuging process.

In a well-known electronic process of measuring hematocrit the pulses to be counted are first weighted in proportion to the volumes of the respective particles being counted. Then the resultant weighted pulses are added, that is, integrated, thereby producing a signal that is proportional to the percent volume of the fluid that is occupied by the particles.

While the invention may be applied in other ways, for simplicity it will be described herein specifically in terms of density or concentration as represented by count per unit volume. Accordingly, it will be understood that the broad concepts that underlie the invention may be applied to density or concentration measured and expressed in other ways than in count per unit volume.

OBJECTS AND SUMMARY OF THE INVENTION

It is a primary object of this invention to provide an improved system for determining the platelet density of an undetermined volume of a blood sample by simultaneously, electronically measuring the quantity of red blood cells and platelets in such a blood sample.

It is also an object of this invention to provide a method and apparatus for determining the platelet count per unit volume of an undetermined volume of a blood sample without also requiring algebraic manipulation of red blood cell and platelet counts.

It is a further object of this invention to provide an apparatus that will electronically and simultaneously count platelets and red blood cells in a diluted undetermined volume of blood and produce separate counts, one corresponding to the number of red blood cells and one corresponding to the number of platelets. It is also an object of this invention that such an apparatus also provide means for automatically terminating the counting process when the red blood cell count reaches a predetermined value, whereby the platelet count displayed indicates directly the platelet count per unit volume, making algebraic manipulation of the data unnecessary.

It is a further object of this invention to improve the accuracy of the particle counts by circuits that are less likely to inadvertently produce pulses in response to spurious signals, such as noise, and by circuits that count the first of two particles that are detected almost simultaneously even when the first one detected is the smaller of the two particles.

It is a still further object of this invention to provide for automatic termination of the counting process upon occurrence of a predetermined condition.

It is a still further object of this invention to provide a system that automatically takes into account the fact that the number of pulses generated by passing a stream of particles through a particle sensing transducer may be in error because of coincidence effects.

In the specific embodiments of the invention considered in detail herein, a circuit is provided that discriminates electrical signals generated as a result of the detection of platelets, from electrical signals generated as a result of the detection of red blood cells, and also through the provision of a circuit that separately counts electrical pulses generally corresponding to detected platelets and electrical pulses generally corresponding to detected red blood cells until the number of the latter pulses counted reaches a predetermined value, and then automatically stops the platelet counting process whereby the count of pulses generally corresponding to platelets detected or the corresponding platelet count per unit volume, may be automatically displayed as such.

A highly advantageous feature of a preferred embodiment of the present invention resides in the provision of circuit means which permits the application of modern high-speed electronic counting devices for determining platelet count per unit volume directly, thus obviating the usual requirement for subsequent algebraic manipulation otherwise required.

Another highly advantageous feature of a preferred embodiment of the present invention resides in the provision of counting termination means which may be set to any known red blood cell count density at which the electronic counting will be automatically stopped.

Still another highly advantageous feature of this invention is that the accuracy of dilution of the sample is rendered non-critical because the measurement is independent of sample volume. This feature is particularly advantageous because of the preferred use of a sheath that focuses, or confines, the sample stream to the central part of the particle transducer in some embodiments of the invention as explained below.

Other objects, features, and advantages of the invention will be best understood from the following detailed description, taken in conjunction with the accompanying drawings in which:

BRIEF DESCRIPTION OF THE DRAWINGS

FIG. 2 is a block diagram indicating the manner in which FIGS. 2A, 2B, 3 and 4 are to be combined;

FIGS. 2A and 2B are schematic block diagrams of a preferred embodiment of the pulse generating portion of the invention;

FIG. 3 is a schematic block diagram of the counter and display portion of the apparatus shown in FIG. 1;

FIG. 4 is a schematic block diagram of an alternative circuit for use in the red blood cell counter of the invention;

FIG. 8 is a block diagram of an alternative embodiment of the invention; and

FIG. 9 is a detailed schematic of FIG. 8.

GENERAL DESCRIPTION

Figure 1:
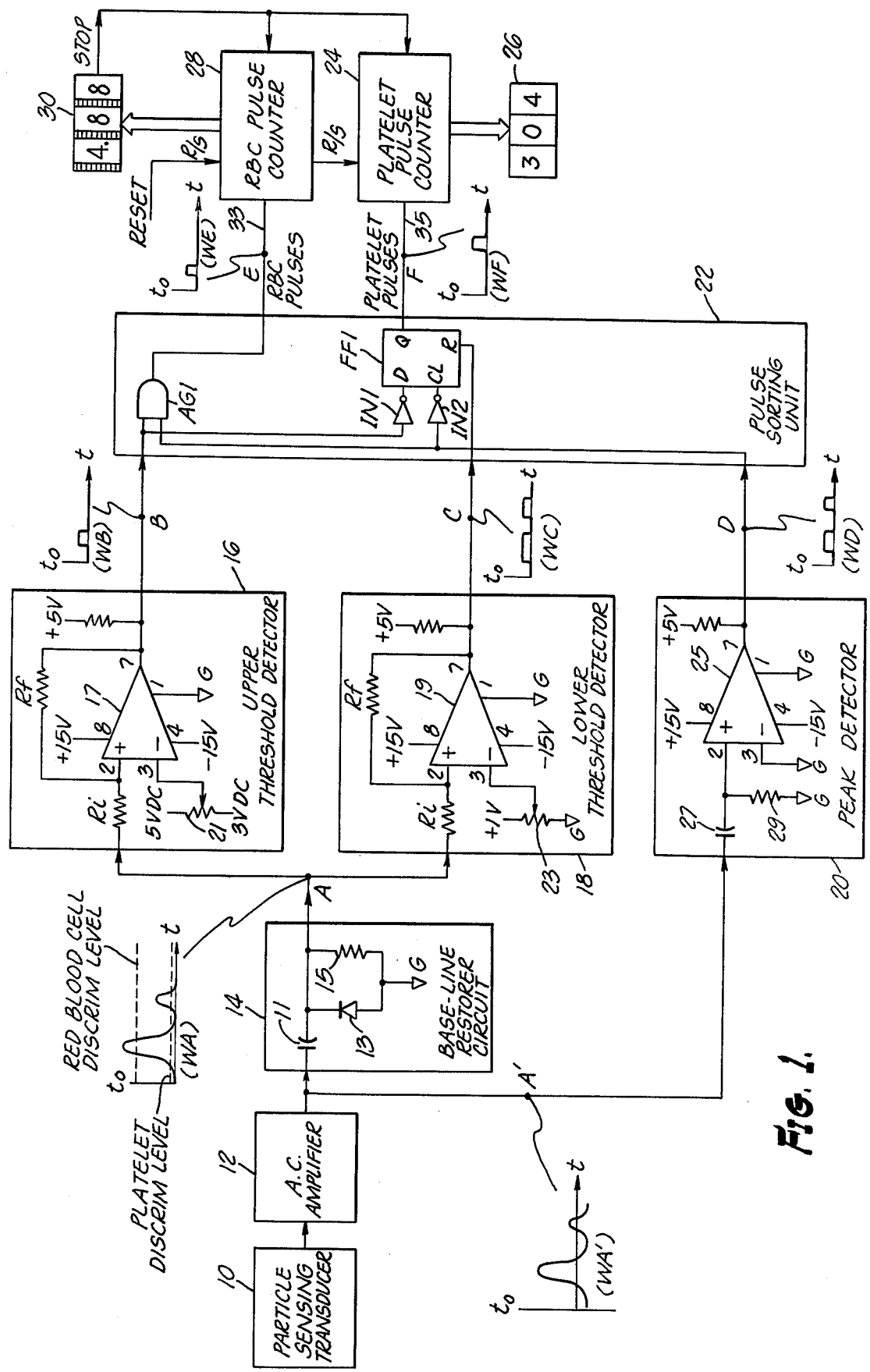
FIG. 1 is a schematic block diagram of a particle ratio calculation apparatus suitable for carrying out the method of this invention for the purpose of determining blood platelet count density.

Referring to FIG. 1, a platelet counting apparatus is generally disclosed as comprising a particle sensing transducer 10 through which a diluted sample of blood is passed to produce a stream of electrical signals having amplitudes that are correlated to some physical characteristic of the particles detected.

The difference in sizes of red blood cells and platelets provides a relatively convenient physical characteristic for discriminating between such particles. There are numerous well-known methods and devices for producing electrical signals that have amplitudes that depend on the sizes of particles suspended in a fluid, such as red blood cells and platelets suspended in diluted whole blood. The relative change in electrical impedance between a pair of electrodes suspended in a conductive fluid as a particle passes through an aperture somewhat larger than the diameter of the particle, is one such well-known method. Other methods, including the use of photodetectors, are also well known.

The particle sensing transducer 10 may be any of such well-known devices as long as it produces an electrical signal, a characteristic of which depends upon the size of the particle being detected. In the best embodiment of the invention now contemplated, the particle sensing transducer is one of the type that produces an electrical signal that has an amplitude that is substantially proportional to the size of the particle being detected.

Furthermore, the particle sensing transducer should preferably be one that avoids problems associated with recirculation of particles after they have passed through the sensing zone of the transducer. A problem of that type, if not eliminated, would make it difficult or even impossible to accurately count particles of different sizes suspended in the same sample. By way of example, one such preferable transducer is disclosed in U.S. Pat. No. 3,902,115 to Hogg. Another suitable transducer is that disclosed in an article entitled "Fluorescence-Activated Cell Sorting", by Herzenberg, Sweet, and Herzenberg, appearing at pages 108 through 117 of Vol. 234, No. 3, *Scientific American,* March, 1976. Still another transducer suitable for this invention, and for also avoiding the abovementioned problem, is described in an article entitled "Electrical Sizing and Counting of Platelets in Whole Blood" by Schultz and Thom, pages 447 through 454, *Medical and Biological Engineering,* July, 1973.

In practice, the number of pulses generated by a transducer of the type mentioned above, as a stream of particles flow through the sensing zone, is less than the number of particles that flow through the sensing zone. One reason for this is that two or more particles may flow through the sensing zone in close proximity to each other thereby producing overlapping pulses, such as two partially overlapping pulses or even only a single pulse. Thus, where two types of particles of different sizes are to be detected, the presence of one particle may produce a pulse that may mask a pulse due to the presence of another particle. This invention reduces errors that might otherwise arise because of such masking or other coincidence effects. But to simplify the explanation of the invention, it will be assumed initially that particles flow through the sensing zone without such interference and then an embodiment of the invention will be described in which many of such masking effects occur but are eliminated or at least reduced and then it will be shown that all embodiments of the invention usually greatly reduce though they may not completely eliminate errors that might otherwise arise because of coincidence effects. In any event, in the practice of this invention in its best form, errors in counting pulses that have their origin in coincidence phenomena are rendered insubstantial.

It is well known that red blood cells and platelets are not of uniform size. In fact, the sizes of each kind of cell are widely distributed and overlap to a small extent. For convenience of explanation, unless otherwise indicated, the invention will be described herein as if the overlap is negligible and can be disregarded.

The signal produced by the particle sensing transducer 10 typically requires amplification before it can be used with readily available commercial components such as those that operate in a voltage range of 0 to 15 volts. A simple alternating current amplifier 12 may be used, typically having a voltage gain of about 2,000 and a bandwidth of about 50 kHz for particle sensing transducers of the impedance changing type. An AC amplifier is preferable since any direct current (DC) voltages that may be generated by the particle sensing transducer do not provide information regarding particle size and might otherwise interfere with operation of the discrimination circuits that are used to differentiate between particles of different sizes, as explained below.

Upper threshold detector 16 and lower threshold detector 18 are used to distinguish pulses corresponding to platelets from pulses corresponding to red blood cells and also to distinguish such pulses from low level noise that might otherwise be inadvertently counted.

To simplify the threshold detection operation, the lower excursion limits of platelet and blood cell electrical signals are clamped to ground. This clamping is accomplished by means of a base-line restorer circuit 14. Peak detector 20 provides means for detecting the peaks of the platelet and red blood cell electrical signals and for providing timing signals whereby the output signals of the upper threshold detector and lower threshold detector can be sampled at about the time of the occurrence of the peak amplitude of the electrical signal.

The combination of AC amplifier 12 and base-line restorer circuit 14 also serves to make the counting operations relatively insensitive to base-line instability in the particle sensing transducer. Base-line instability, that is, random changes in the quiescent operating voltage, may occur, for example, in fluid conductivity devices because of bubble formation.

Pulse sorting unit 22 receives the output signal of upper threshold detector 16, lower threshold detector 18, and peak detector 20, respectively, and in response thereto generates pulses on one of two lines 33 and 35 corresponding to the type of particle that is being detected, either a red blood cell or a platelet. Thus, the pulse sorting unit 22 converts each electrical signal generated by detection of a particle either to a pulse corresponding to a red blood cell or to a pulse corresponding to a platelet and transfers such pulses to counters over separate lines, a first pulse line 33 used exclusively for red blood cell pulses and a second pulse line 35 used exclusively for platelet pulses.

As shown on the right side of FIG. 1, the two pulse lines 33 and 35 from the pulse sorting unit 22 are connected to separate counters. The platelet pulse line 35 is connected to a platelet pulse counter 24 and the red blood cell pulse line 33 is connected to a red blood cell pulse counter 28. Since each counter will be activated only by those pulses corresponding to the particular type of particle to which it is assigned, the count produced by each counter will correspond only to the number of particles of that type. Therefore, the red blood cell pulse counter counts the number of red blood cells passed through the particle sensing transducer 10 and the platelet pulse counter 24 counts the number of platelets passed through the particle sensing transducer 10.

As also indicated on the right side of FIG. 1, the platelet pulse counter 24 is connected to a platelet display unit 26 wherein the platelet count produced may be displayed and thus observed by a user. On the other hand, the output of the red blood cell pulse counter 28 is connected to a register in the form of a thumbwheel switch array 30 which will have been set to a predetermined count corresponding typically to a previously known or assumed red blood cell count per unit volume of the blood sample being tested. When the output of the red blood cell pulse counter 28 corresponds to the preset count that has been set into thumbwheel switch array 30, a count terminating signal STOP is generated to automatically and immediately terminate the counting processes taking place in red blood cell pulse counter 28 and platelet pulse counter 24. The number of red blood cells counted will then be equal to the preset value set into thumbwheel switch array 30 and the platelet pulse counter will display the number of platelets that have been simultaneously counted. The platelet display will then correspond to the number of platelets per unit volume in the sample used to count the red blood cells.

Figure 2:
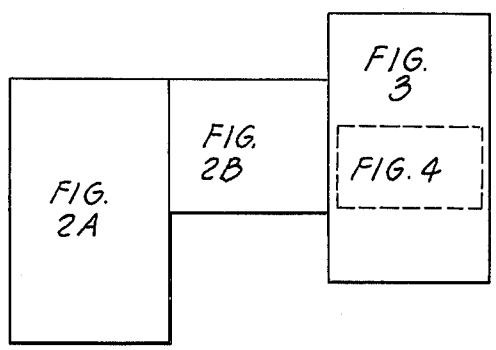
Figure 2A:
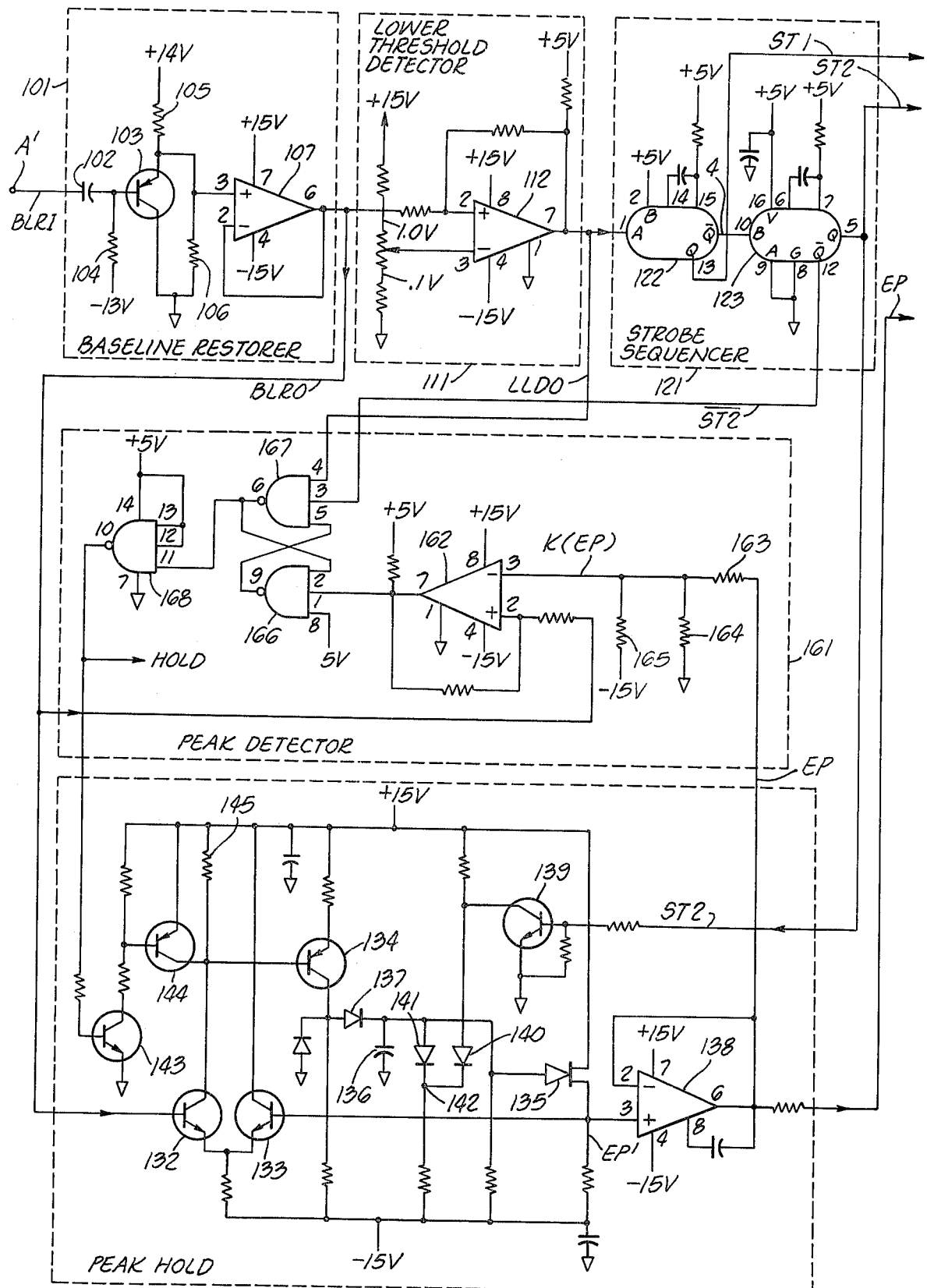

Although the embodiment of FIG. 1 is suitable for practicing this invention, there are certain additional advantages which, under some laboratory situations, may be deemed to be desirable and which are provided by means of the preferred embodiment of the circuit of this invention disclosed in FIGS. 2A and 2B. By way of example, the circuit of FIG. 2A employs a baseline restorer circuit that also serves as a high pass filter to reduce the circuit sensitivity to lower frequency noise signals, such as 60 cycle alternating current. By way of further example, an embodiment of this invention that utilizes the circuit of FIG. 2A is even less likely to produce an erroneous number of pulses in response to noise signals superimposed upon the output signals of the sensing transducer. And furthermore, the circuit of FIG. 2A is more likely to generate a platelet pulse corresponding to a platelet that is detected just prior to and almost coincident with a red blood cell. The circuit of FIG. 2A therefore avoids the otherwise inherent masking effects of larger red blood cells in the counting procedure. These and other advantages of the circuit of FIGS. 2A and 2B will be more fully appreciated from a reading of the detailed description of the various embodiments of this invention disclosed herein.

In the best mode of practicing the invention now contemplated, the count terminating signal STOP is employed to terminate the two counting operations taking place. However, the main advantages of the invention would be attained even if only the platelet counting operation was terminated and even if neither counting operation was stopped, as long as the platelet count produced when the preset red blood cell count is reached, is made available to the user.

In preferred embodiments of the method and apparatus of this invention, the red blood cell concentration of the sample under test will be already known and the sensing transducer will employ a sheath focusing system. Such a system is disclosed and claimed in copending application Ser. No. 780,402, filed Mar. 23, 1977, in the name of John L. Haynes, entitled "Apparatus for Counting Particles in a Liquid Suspension" and assigned to the present assignee. In flow systems such as those most suitable for use in the invention, namely, those involving the accurate measurement of particle size and count, it is desirable to use a focused system where a core of sample fluid flows in the center of a sheath of particle-free fluid. Such a system can project the sample accurately along the center of the sensing region. However, in such a system it is very difficult to proportion the relative volume of sample and sheath because the sheath focusing system causes an uncontrolled sample dilution. This uncontrolled dilution precludes measuring sample-flow volume, since the flow volume measured would be for an unknown proportion of sample and sheath and since in such a focused system volume and flow rate are typically about 50 times smaller than in an unfocused system.

In a focused system, sample volumes of 10 to 30 microliters and flow rates of 0.1 to 0.5 microliters per second are typical. Equipment to measure such small volumes and flow rates is difficult to make accurate, reliable, and inexpensive. Utilizing this invention, however, and a prior knowledge of the particle density, or concentration, of one of the constituent particles of the sample, it is possible to ascertain the particle density, or concentration, of other types of constituent particles of the sample. The only condition is that the various types of particle be distinguishable by some physical characteristic from each other. Furthermore, particle concentrations can be ascertained despite an uncontrolled dilution ratio and an unknown and small sample flow rate.

In this invention, use is normally made of prior knowledge about one of the constituent particles of a sample under test. In the event that such prior knowledge is not available, it is possible to first use the same transducer without a sheath to accurately measure the density, or concentration, of one of the constituent particles before proceeding with the simultaneous counting of all the constituent particles of the sample.

Furthermore, in the event that prior knowledge about one of the constituent particles of the sample is not available, this invention also contemplates the additional step of mixing with the sample under test, a second sample containing a known density of some physically distinguishable particles. Although the mixing of the initial samples must be precise, subsequent sampling and dilutions of the mixture need not be precise. As a result, the previously discussed problems of simultaneous counting of particles of different sizes while using a front sheath, are overcome in this embodiment of the invention. The particles of the second sample may be any particles suitable for sensing in a sensor zone of the transducer as long as they are distinguishable from particles of unknown concentration that may be in the sample. Synthetic particles of known size and in known concentration are typically suitable for such purposes. For example, a polyethylene or polystyrene bead manufactured by Dow Corning of Midland, Michigan, would be an appropriate synthetic particle for blood sample measurements made by means of this invention.

DETAILED DESCRIPTION

In this detailed description of the invention, apparatus and method for discriminating between pulses generated as a result of detecting platelets and pulses generated as a result of detecting red blood cells, and for counting such pulses, are described in sufficient detail to enable one of ordinary skill in the art to build the apparatus and to practice the method in accordance with the best mode presently contemplated. The particle sensing transducer 10 and the AC amplifier 12 indicated in FIG. 1, are each well known in the art and no further description of either is required. It need only be noted that the passage of a sample volume of whole blood through the particle sensing transducer 10 will produce electrical signals at the output of AC amplifier 12 such as those indicated in waveform WA' of FIG. 1. Waveform WA' corresponds to electrical signals that would appear at circuit point A', which are the output signals of the AC amplifier 12 when a red blood cell and then a platelet are detected by the particle sensing transducer 10.

In FIG. 1 the shape of the waveform WA' corresponds to changes in resistances that occur between electrodes of the transducer 10 as the sample flows therethrough. As indicated, pulses of different height are produced depending upon whether a red blood cell or a platelet is detected. In one modification of the invention, the electrical signal is differentiated and again the relative heights of the pulses in the resultant waveform are detected. In the waveform WA' illustrated, large pulses correspond to red blood cells and small pulses correspond to platelets. After differentiation the relative heights of the pulses in the differentiated signal are maintained, small pulses corresponding to platelets and large pulses corresponding to red blood cells. Thus other characteristics of pulses that correspond to different particles may be employed in the practice of the invention. But for simplicity, the invention will be described in detail only with reference to an electrical signal of the type represented by the particular waveform WA'.

Base-line restorer circuit 14 comprises a series capacitor 11, and a diode 13, and a resistor 15 connected in parallel between point A and ground G, as shown in FIG. 1. As previously indicated, the purpose of base-line restorer circuit 14 is to restore the 0 volt DC base line to the AC coupled output signals of the AC amplifier 12, so that the threshold voltage detectors 16 and 18 can be used more conveniently.

The output signal of the base-line restorer circuit 14 for the input signal corresponding to waveform WA', corresponds to waveform WA, namely, two pulses, the larger one corresponding to the earlier detected red blood cell, and the smaller one corresponding to the later detected platelet, and a common base line at approximately 0 volts DC. The reference time "$t_o$" in each of the waveforms is the same and is intended to provide a rough indication of the relative time relationships of all of the waveforms WA', WA, WB, WC, WD, WE, and WF, shown in FIG. 1.

Upper threshold detector 16 and lower threshold detector 18 employ voltage comparators 17 and 19, respectively. The two threshold detectors 16 and 18 are identical in all respects with the exception of the voltages applied to potentiometers 21 and 23, respectively. Potentiometer 21 of upper threshold detector 16 is connected at a first end to a voltage source of about 3 volts DC and at a second end to a voltage source of about 5 volts DC, whereby the voltage with respect to ground at the arm of potentiometer 21 may be made to vary between 3 volts DC and 5 volts DC. On the other hand, potentiometer 23 of lower threshold detector 18 is connected at a first end to a voltage source of about 1 volt DC and at a second end to ground, whereby the voltage with respect to ground at the arm of potentiometer 23, may be made to vary between 0 volts DC and 1 volt DC. In this case the two voltage ranges do not overlap.

Each threshold detector 16 or 18 employs a voltage comparator which is a high gain amplifier 17 or 19, respectively as the case may be, the output signal of which is driven to a high limit when the input voltage applied to the positive input line at terminal 2 exceeds the reference voltage applied to the negative input line at terminal 3, and is driven to a low limit when the opposite occurs. One such voltage comparator is a National Semiconductor Model LM311 Voltage Comparator/Buffer which is described at pages 3-21 through 3-25 of the National Semiconductor publication entitled "Linear Integrated Circuits", (1975 edition).

Terminals 4 and 8 of each voltage comparator are connected to −15 volts DC and +15 volts DC, respectively, and terminal 1 of each voltage comparator is connected to ground G. Output terminal 7 of each comparator is connected by means of a feedback resistor $R_f$ to the input terminal 2. This feedback arrangement, including input resistor $R_i$, increases the precision with which the voltage difference between the positive and negative input lines drives the output signal from one limit to the other.

In FIG. 1 the waveform WB represents the electrical signal developed at point B in response to the application to the detector 16 of input signals of the waveform WA corresponding to circuit point A. Waveform WB is a single pulse that has a width that corresponds to the portion of the red blood cell detection signal that exceeds the upper threshold level set in the upper threshold detector 16 by means of the potentiometer 21. The electrical signal that corresponds to the detection of a platelet, produces no corresponding output signal at point B because the amplitude of the platelet pulse is below the red blood cell discrimination level of upper threshold detector 16.

Also in FIG. 1, waveform WC represents the output signal of lower threshold detector 18. Waveform WC includes two electrical signals or pulses, one developed as a result of the red blood cell signal exceeding the platelet discrimination level and the other resulting from the platelet signal exceeding that level. Since the electrical signals developed by detection of the respective particles, both exceed the platelet discrimination level, two pulses are generated at the output of lower threshold detector 18. Note that the pulse corresponding to the red blood cell electrical signal is greater in width. This greater width occurs because the period of time during which the red blood cell electrical signal exceeds the platelet discrimination level, is greater than the period of time in which the platelet signal exceeds that level.

Peak detector 20 comprises a voltage comparator 25 which may also be a National Semiconductor LM311, the same as the voltage comparator that is suitable for use in the threshold detectors 16 and 18. Terminal 3 of the voltage comparator 25, the negative voltage input line, is connected to ground reference G. The input line to the positive voltage terminal of the voltage comparator 25 includes a series capacitor 27, and a parallel resistor 29 connected to ground G. The capacitor and resistor together comprise a simple differentiator circuit which, as is well known, generates a non-zero output signal only when the input signal is changing and generates a zero output signal only when the input signal is constant. Since the input signals for detected red blood cells and platelets have a positive slope, a zero slope, and then a negative slope, in that order, the differentiator circuit first generates a positive signal during the positive slope transient period, a zero output during the zero slope period, and a negative signal during the negative slope transient period of the input signal. The output signal of the voltage comparator 25 is shown in FIG. 1 as waveform WD which corresponds to the signal appearing at point D for an input waveform WA'. As indicated in waveform WD, the output signal of the peak detector 20 is a positive signal during the positive slope period of the red blood cell pulse and a positive signal during the positive slope period of the platelet pulse and zero at all other times. In this embodiment, the purpose of the peak detector is to provide timing signals that indicate the approximate time of occurrence of the peak of the electrical signal generated by detection of particles. Offset balancing of the type shown on page 3-21 of the aforementioned publication of National Semiconductor, Inc., may be employed to adjust the voltage comparator so that it produces an output signal voltage when the differential input voltage is just above zero volts.

The purpose of the upper threshold detector 16, lower threshold detector 18, and peak detector 20, is to generate signals that are used to distinguish between electrical signals generated by detection of red blood cells and electrical signals generated by detection of platelets, and to produce pulses on separate lines 33 and 35 that are counted separately, one set of pulses on a first line 35 corresponding only to platelets and another set of pulses on a second line 33 corresponding only to red blood cells. The conversion of the signals generated in detectors 16, 18, and 20 to separate pulses applied to separate lines 33 and 35, is accomplished in the pulse sorting unit 22.

Pulse sorting unit 22 is comprised of an AND-gate AG1, two logic inverters IN1 and IN2, and a D-type flip-flop FF1. An AND-gate produces a ONE, or TRUE, output signal (e.g., +5 volts DC) only when ONE, or TRUE, input signals are applied simultaneously to the respective input lines of the AND-gate. An AND-gate produces a ZERO, or FALSE, output signal (e.g., 0 volts DC) at all other times. A logic inverter produces a ONE, or TRUE, output signal when the input signal is ZERO, or FALSE, and it produces a ZERO, or FALSE, output signal when the input is ONE, or TRUE. The Q terminal of a D-type flip-flop produces a ZERO, or FALSE, output signal as long as a ZERO, or FALSE, signal is applied to the reset terminal R. However, when the signal applied to the reset terminal R is a ONE, or TRUE, signal, the Q terminal produces, at each occurrence of the edge of a positive going clock signal CL, a signal that has a logic state that is the same as the logic state of the signal that is applied to data terminal D.

The output signals of the upper threshold detector 16 and the peak detector 20, are each applied to the two input-lines of AND-gate AG1. Accordingly, AND-gate AG1 will generate a ONE output signal only when the signals appearing at points B and D are simultaneously positive voltages. Thus, a pulse corresponding to the detection of a red blood cell will be produced at the output of AND-gate AG1 corresponding to red blood cell pulse line 33 when, at about the occurrence of the peak of the detected signal, the amplitude of that detected signal exceeds the upper threshold level that has been set in upper threshold detector 16.

As shown in FIG. 1, pulse sorting unit 22 employs an inverter IN1 to apply an inverted form of the output signal WB of the upper threshold detector 16 to the data terminal D of flip-flop FF1. Another inverter IN2 is employed to apply an inverted form of the peak detector output signal WD to the clock terminal CL of flip-flop FF1. As also shown, the output signal WC of lower threshold detector 18 is applied to the reset terminal R of flip-flop FF1. The output terminal Q of flip-flop FF1 is tied directly to platelet pulse line 35 so that the Q output of flip-flop FF1 determines the status of the signal appearing on platelet pulse line 35.

If the detected input signal WA does not exceed the lower threshold level, the reset terminal R of flip-flop FF1 is held FALSE thereby preventing the output signal WF on terminal Q of flip-flop FF1 from becoming TRUE. On the other hand, if the signal on the output of lower threshold detector 18 is TRUE, as a result of a detected input signal that exceeds the lower threshold level, the reset terminal R of flip-flop FF1 is set to a TRUE level. Thereafter, while the ONE, or TRUE, signal is applied to the reset terminal R of flip-flop FF1, output terminal Q produces an output signal that has the same logic state as that of the signal applied to the data terminal D, at the occurrence of a positive-going signal applied to the clock terminal CL of flip-flop FF1.

If a detected signal WA exceeds the lower threshold level of lower threshold detector 18, and also exceeds the upper threshold level of upper threshold detector 16, the flip-flop FF1 is enabled and the input signal applied to the data terminal D of flip-flop FF1 is FALSE. Therefore, when the peak detector 20 produces an output signal at or about the occurrence of the peak of the detected signal, the flip-flop FF1 will be clocked and an output signal having a FALSE logic state corresponding to the FALSE logic state applied to the data input terminal D of flip-flop FF1 appears at the output terminal Q. As previously indicated, the AND-gate AG1 will, on the other hand, produce a signal WE having a TRUE logic state. Therefore, when a red blood cell is detected, a pulse corresponding to the presence of a detected red blood cell is applied to red blood cell line 33 and no pulse is applied to the platelet line 35.

Alternatively, if the detected signal has an amplitude that exceeds the lower threshold level of lower threshold detector 18, but falls below the upper threshold level set for upper threshold detector 16, the signal applied to the data terminal D of flip-flop FF1 will be TRUE after it is inverted by inverter IN1. Therefore, at the occurrence of the next peak detector pulse generated by peak detector 20, that is applied to the clock terminal CL of flip-flop FF1, a TRUE output signal corresponding to a platelet pulse applied to platelet pulse line 35 will appear at the output terminal Q of flip-flop FF1. Concurrently, AND-gate AG1 produces a FALSE signal because the signal on one of the two input lines to AND-gate AG1 is FALSE, namely, the signal on the line connected to the output of the upper threshold detector 16. Therefore, when an electrical signal is produced corresponding to a detected platelet, only a platelet pulse is produced and no red blood cell pulse is produced for that signal.

In this way, each detected particle that satisfies the threshold criteria is counted either as a red blood cell or as a platelet, depending on which criterion is satisfied. However, it will be seen below in conjunction with the discussion of FIGS. 6 and 7 that in some embodiments it is possible and desirable to produce a count increment for both types of particles even though only one type is detected. It may be also possible and desirable in such embodiments to produce no count increment for either type of particle even though one or both types are detected in a restricted size range.

AND-gate AG1 in pulse sorting unit 22 may be a 2-input, positive TTL AND-gate, such as that available in the Quadruple 2-Input Positive AND-gate Model No. SN7408 manufactured by Texas Instruments, Inc. The inverters IN1 and IN2 may be any common TTL inverter, such as those in the HEX Inverter Model No. SN7404 manufactured by Texas Instruments, Inc. The flip-flop FF1 may be any TTL Type-D flip-flop unit, such as No. SN7474.

ALTERNATIVE EMBODIMENT

The circuit of FIGS. 2A and 2B represents an alternative embodiment of the detection and pulse sorting portion of the apparatus of this invention.

The circuit of FIGS. 2A and 2B would be a direct replacement for the portion of the circuit of FIG. 1 between circuit point A' and circuit points E and F. FIG. 2 shows how FIGS. 2A and 2B are to be combined with each other and with FIG. 3 or alternatively, with each other and with a combination of FIG. 3 and FIG. 4.

BASELINE RESTORER CIRCUIT

Baseline restorer circuit 101 serves the same purpose previously described in conjunction with baseline restorer circuit 14 of FIG. 1, namely, to clamp the AC-coupled waveform produced by AC amplifier circuits (not shown in FIG. 2), to approximately 0 volts DC thereby making it more convenient to discriminate pulses on the basis of their amplitudes. As indicated in FIG. 2A, baseline restorer circuit 101 comprises a high pass filter circuit, including a capacitor 102, a PNP transistor 103 oriented in a modified common collector, or emitter follower configuration and biased into saturation by resistors 104, 105, and 106, and an amplifier 107. Amplifier 107 serves as a buffer, or isolation device, permitting the application of the output signal BLRO of baseline restorer circuit 101 to a number of other circuits. The input signal to the baseline restorer circuit 101 is designated BLRI.

Figure 5:
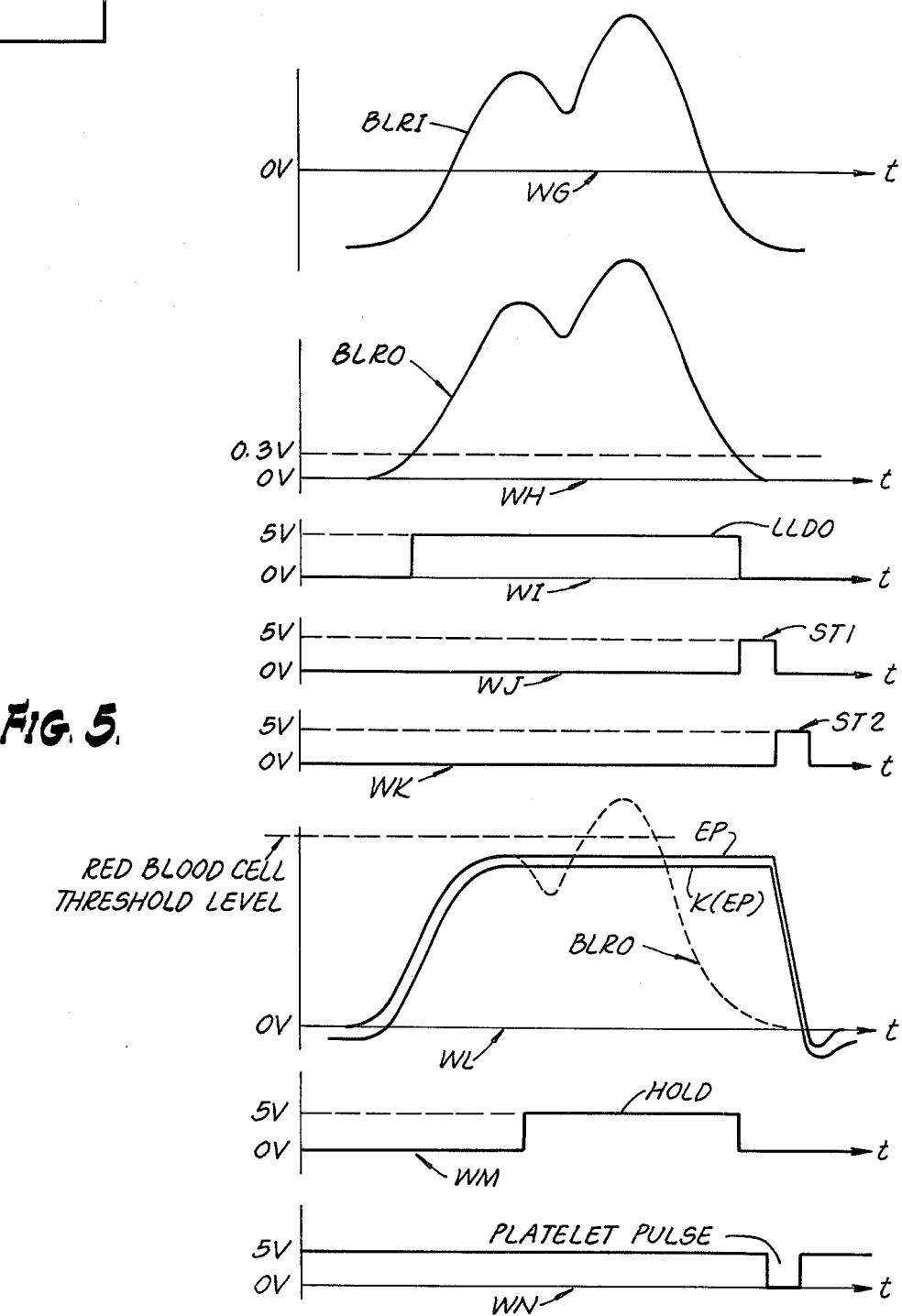
FIG. 5 is a timing diagram showing the timing relationships of various waveforms corresponding to FIGS. 2A and 2B.

The particular common collector configuration of transistor 103 provides a high input resistance to base current flowing toward the base-collector junction, and low resistance to base currents flowing away from the base-collector junction and toward capacitor 102. Accordingly, the capacitor-transistor combination of baseline restorer circuit 101 provides a DC clamp to 0 volt DC. Waveforms WG and WH of FIG. 5 show a typical input signal BLRI and a typical output signal BLRO respectively, illustrating the clamping operation of the baseline restorer circuit 101. Baseline restorer circuit 101 also serves as a high pass filter which filters out low frequency signals, such as 60 Hz AC signals that would otherwise reduce the detection and counting reliability of the apparatus. Amplifier 107 may be a Motorola Model MC1741S high slew rate, internally compensated, operational amplifier manufactured by Motorola Incorporated, Phoenix, Arizona.

LOWER THRESHOLD DETECTOR

As indicated in FIG. 2A, the output signal BLRO of the baseline restorer circuit 101 is applied to a lower threshold detector circuit 111 which includes voltage comparator 112 and which is similar to that previously described in conjunction with FIG. 1 and therefore need not be described again at this point. The output signal LLDO of lower threshold detector circuit 111 of FIG. 2A, is dependent upon whether or not the amplitude of the input signal, namely, baseline restorer circuit output signal BLRO, exceeds the amplitude of the reference voltage applied to the second input terminal of voltage comparator 112. Waveform WI of FIG. 5 shows output signal LLDO for the applied signal BLRO of waveform WH.

STROBE SEQUENCER CIRCUIT

The output signal LLDO of lower threshold detector 111 is applied to strobe sequencer circuit 121 which comprises a pair of one-shot devices, that is, monostable multivibrator devices 122 and 123, such as the one-shot devices provided in a Texas Instruments Model 74123 Dual Retriggerable Monostable Multivibrator. Strobe sequencer 121 develops strobe signals ST1, ST2, and $\overline{ST2}$, which are used in the circuit for timing and for resetting the pulse generating and detection operation of the embodiment of the invention shown in FIGS. 2A and 2B. Details of the manner in which the strobe signals generated in strobe sequencer 121 are used in the circuit of FIGS. 2A and 2B will be discussed below. Waveforms WJ and WK of FIG. 5 represent the strobe signals ST1 and ST2 generated by strobe sequencer 121 in response to the signal BLRO of waveform WH.

PEAK HOLD CIRCUIT

The output signal BLRO of the baseline restorer circuit 101 is also applied to a peak hold circuit 131. The purpose of peak hold circuit 131 is to develop an output signal EP which, as shown in waveform WL of FIG. 5, follows the BLRO signal and then maintains the first of the two peak levels of signal BLRO, the first peak level corresponding to a detected platelet and the second peak level corresponding to a subsequently detected red blood cell, until the peak hold circuit is reset by a strobe signal ST2 generated in strobe sequencer 121.

Transistors 132, 133, and 134 of the peak-hold circuit 131 in combination constitute a simple differential amplifier, a positive input signal to which is the signal BLRO and the negative input signal to which is the output signal EP' applied to the base terminal of transistor 133 from the source terminal of FET transistor 135. As the output signal BLRO of the baseline restorer circuit 101 increases in voltage level, capacitor 136 of peak hold circuit 131 is charged through diode 137. The voltage across capacitor 136 is applied to the gate terminal of FET transistor 135. FET transistor 135 acts as a unity gain follower device. As seen in FIG. 2A, the source terminal of FET transistor 135 is connected to the positive input terminal of amplifier 138 which may be a Motorola Model MC1741S operational amplifier. Thus, it can be seen that the portion of the peak hold circuit 131 so far described, provides means for charging a capacitor 136 in accordance with an input voltage, thereby producing an output signal EP that will, in effect, track the input signal BLRO as long as it continues to increase, but which, because of blocking diode 137, cannot track the input signal BLRO when it decreases. Waveform WL of FIG. 5 illustrates the tracking and peak retention characteristics of signal EP.

After the signal EP is used to count either a pulse corresponding to a red blood cell or pulse corresponding to a platelet, as the case may be, capacitor 136 may then be discharged so that it is reset and made ready for the next signal corresponding to a subsequently detected particle. The discharge of capacitor 136 is accomplished by means of transistor 139 and the strobe signal ST2 applied to the peak hold circuit 131 by the strobe sequencer circuit 121. The strobe signal ST2 is a positive step waveform of approximately 5 microseconds duration (see waveform WK in FIG. 5). When this signal is applied to the base circuit of transistor 139, the transistor is turned on, thereby grounding the junction 142 between the anodes of diodes 140 and 141 respectively. As a result, the positively charged capacitor 136 is allowed to discharge through diode 141 to about ground potential and the peak hold output signal EP eventually decays to 0 volts, as shown by waveform WL in FIG. 5.

As explained previously, one of the advantageous features of this preferred embodiment of the invention, is that a lower amplitude pulse corresponding to a detected platelet that occurs just prior to a higher amplitude pulse corresponding to a subsequently detected red blood cell, will be more likely counted as a platelet instead of as a red blood cell. This feature of the embodiment of the circuit indicated in FIG. 2A, is made possible by the use of a hold signal HOLD that is applied to the base circuit of transistor 143 of peak hold circuit 131. The manner in which hold signal HOLD is generated, will be described subsequently in conjunction with the description of the peak detector circuit 161. However, at this point, it is sufficient to note that the hold signal HOLD is a positive step waveform (see waveform WM in FIG. 5) that is generated when signal BLRO begins to decrease and falls, by some predetermined level, below its immediately preceding peak level. The hold signal HOLD is applied to the peak hold circuit 131 for the purpose of inhibiting a further increase in the charge across capacitor 136 after the first peak level, satisfying the criterion established for generation of the hold signal, is received by the peak hold circuit 131. In this way, the peak hold circuit is made insensitive to signals that occur immediately subsequent to the first peak, and output signal EP of peak hold circuit 131 retains the lower platelet signal peak and is prevented from increasing inadvertently to the subsequently detected red blood cell signal peak.

When the hold signal HOLD, a +5 volt DC step signal, is applied to the base circuit of transistor 143, transistor 143 is turned on. When transistor 143 is on, the emitter-base juction of transistor 144 becomes forward biased and transistor 144 is also turned on. When transistor 144 is on, resistor 145 is bypassed and the emitter-base junction of transistor 134 is strobed by transistor 144 thereby turning off transistor 134, and preventing capacitor 136 from being charged any further.

Thus, the output signal EP of peak hold circuit 131 is a signal that follows the value of signal BLRO generated by the baseline restorer circuit 101, until it is held at a constant level at the occurrence of the hold signal HOLD. Signal EP may be reset and made ready for a subsequent signal BLRO upon the application of the Strobe signal ST2.

The degree of coincidence of pulses that still permits detection of a first occurring platelet pulse, is determined by the operation of the peak hold circuit 131 in conjunction with the hold signal HOLD, and is dependent on the predetermined level by which the signal BLRO must fall before the hold signal HOLD is generated. Typically it is possible to distinguish a platelet signal having a peak that occurs about 10 microseconds earlier than the peak of a red blood cell signal.

PEAK DETECTOR CIRCUIT

As previously indicated, the purpose of the peak detector circuit 161 is to generate the +5 volt step signal HOLD each time the level of the output signal BLRO falls below its previous maximum by some predetermined amount. In the embodiment of the preferred circuit indicated in FIG. 2A, the hold signal HOLD is generated when the signal BLRO falls below 0.91 $BLRO_{max}$ − 50mv. As shown in FIG. 2A, the peak detector 161 employs a voltage comparator 162 which may be an NSC Model LM311 previously described in conjunction with the threshold detectors of FIG. 1. The output signal BLRO of baseline restorer circuit 101 is applied to the positive input terminal of voltage comparator 162 and a signal K(EP) which is a fixed multiple K of the output signal EP of peak hold circuit 131, is applied to the negative terminal of voltage comparator 162. The factor K is dependent upon the values of series resistor 163 and shunt resistor 164, and is also dependent upon the value of resistor 165 which is connected to −15 volts DC.

In one form of this embodiment, resistor 163 is approximately 10,000 ohms, resistor 164 is approximately 100,000 ohms, and resistor 165 is approximately 3,300,000 ohms. With those values for the resistors 163, 164, and 165, K(EP) is equal to 0.91EP − 50mv. and the output of voltage comparator 162 is +5 volts as long as the output signal BLRO of baseline restorer circuit 101 equals or exceeds K(EP). However, when the voltage level of the signal K(EP) applied to the negative terminal of voltage comparator 162, exceeds the instantaneous level of output signal BLRO, the output signal of voltage comparator 162 changes to 0 volts DC.

The output signal of voltage comparator 162 is applied to one terminal of a three input NAND-gate 166. NAND-gate 166, in combination with NAND-gate 167, forms a set-reset flip-flop circuit. The output signal of the set-reset flip-flop circuit comprising NAND-gates 166 and 167, is applied to one input terminal of a three input NAND-gate 168 that is used as a simple logic inverter. The output of NAND-gate 168 is the hold signal HOLD.

As indicated in FIG. 2A, the second and third input terminals of NAND-gate 168 of peak detector 161, are both tied to +5 volts DC. Therefore, the output signal of NAND-gate 168 is dependent upon the logic level of the output signal of the set-reset flip-flop comprising NAND-gates 166 and 167. Since NAND-gate 168 inverts the logic level of its input signals, a HIGH-level hold signal HOLD will be produced when the output signal of the set-reset flip-flop circuit is LOW. However, the output signal of the set-reset flip-flop circuit can be LOW only when the output signal of NAND-gate 166 is HIGH and the signals on input terminals 3 and 4 of NAND-gate 167 are both HIGH. The signal applied to input terminal 4 of NAND-gate 167 is the output of lower threshold detector 111 which prevents the hold signal HOLD from being generated when the output signal BLRO of baseline restorer circuit 101 is less than the 300 mv. threshold level. Otherwise, the output signal EP of peak hold circuit 131 might be held at a level corresponding to a noise signal which might be counted erroneously as a detected platelet at the occurrence of the next pulse, even though that next pulse might actually correspond to a detected red blood cell.

A third input signal to NAND-gate 168 is Strobe signal $\overline{ST2}$, a signal developed by strobe sequencer 121 which is the logic inverse of the Strobe signal ST2 previously described in conjunction with the peak hold circuit 131.

Strobe sequencer circuit 121 includes monostable multivibrators (also called one-shots 122 and 123). The pulse generated by each one-shot is nominally about 5 microseconds in duration. The Strobe signal is also used to reset the output signal EP of peak hold circuit 131, and the Strobe signal $\overline{ST2}$ is an input signal to NAND-gate 167 of peak detector circuit 161.

UPPER THRESHOLD DETECTOR

The three signals, Peak Hold Output signal EP, strobe signal ST1 and Strobe signal ST2, are applied to the circuits shown in FIG. 2B. Signal EP is applied to the positive input of upper threshold detector 171 which comprises a voltage comparator 172 and operates in a manner previously discussed in conjunction with FIG. 1. The voltage applied to the negative terminal 3 of comparator 172, is the reference potential against which signal EP is compared. Nominally, this reference potential is about 3.5 volts DC which corresponds to the threshold level for typical minimum red blood cell size.

PULSE SORTING UNIT

The output signal of upper threshold detector 171 is applied to the data terminal D of a D-type flip-flop 182 in pulse sorting unit 181. The strobe signal ST1 is applied to the clock terminal CL of the same flip-flop 182. Output terminal Q of flip-flop unit 182 is connected to one input terminal of a dual-input NAND-gate 183, and output terminal $\overline{Q}$ of flip-flop unit 182, is connected to one input terminal of a dual-input NAND-gate 184. The strobe signal ST2 is connected to each of the other input-terminals of NAND-gates 183 and 184 respectively.

If the signal EP generated at the output of peak hold circuit 131 shown in FIG. 2A, exceeds the threshold level established for minimum size red blood cells, the output signal of upper threshold detector 171 shown in FIG. 2B, will be approximately +5 volts DC. As a result, upon the subsequent occurrence of a positive strobe signal ST1, the output terminals Q and $\overline{Q}$ will present positive and negative, that is, HIGH and LOW signals respectively to NAND-gates 183 and 184. However, with strobe signal ST2 normally at 0 volts DC, the output terminals of NAND-gates 183 and 184 will both produce a High logic level signal, until strobe signal ST2 goes positive, at which point the output signal of NAND-gate 183 will change from a High level voltage to a Low level voltage, and the negative going edge of the signal on pulse line 33 will be counted as a red blood cell pulse.

On the other hand, if the signal level of output signal EP of the peak hold circuit 131 is less than 3.5 volts, corresponding to a detected platelet, the output signal of upper threshold detector 171 will be about 0 volts DC and upon application of the Strobe signal ST1 to the clock terminal CL of D-type flip-flop 182, output terminals Q and $\overline{Q}$ of flip-flop 182 will produce negative and positive, that is, Low and High level voltages respectively. Thereafter, receipt by pulse sorting unit 181 of a High level strobe signal ST2, will change from positive to negative, that is, from High to Low level, the output of NAND-gate 184 on pulse line 35 (see waveform WN of FIG. 5). Accordingly, a platelet pulse will be counted.

It will be noted that the pulse sorting unit of FIG. 1 produces positive-going pulses for detected platelets and red blood cells, while the pulse sorting unit of FIG. 2 produces negative-going pulses corresponding to detected red blood cells and platelets. However, as will be understood below as a result of a detailed description of the counting circuits of this invention, in conjunction with FIGS. 3 and 4, the counting circuits of the embodiment illustrated respond to the negative-going edges of the pulses, and therefore will count either the returning edge of the positive pulse or the beginning edge of the negative pulse. It is not intended to limit the scope of this invention to any particular voltage polarity or magnitude.

COUNTING CIRCUITS

Figure 3:
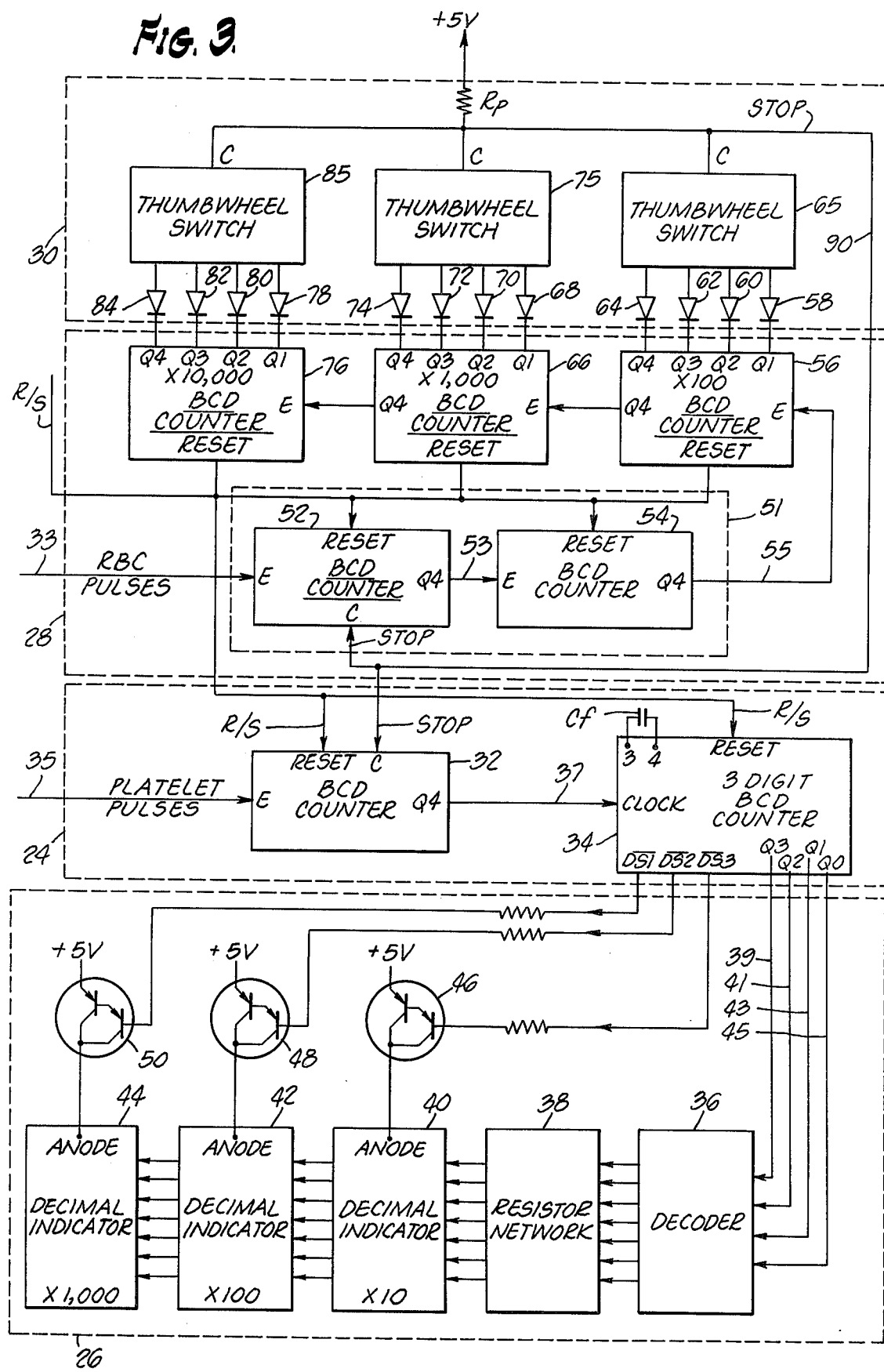

FIG. 3 provides a detailed diagrammatical view of the counting portion of the invention, that counting portion comprising platelet pulse counter 24, platelet count display unit 26, red blood cell pulse counter 28, and thumbwheel switch array 30.

Pulses corresponding to detected platelets are transferred from the pulse sorting unit 22 of FIG. 1 or 181 of FIG. 2B to the platelet pulse counter 24 over line 35 where they are applied to the enable terminal E of a binary coded decimal counter 32. The binary coded decimal counter 32 produces one positive pulse at its output terminal Q4 for each ten platelet pulses transferred to it over line 35. A Motorola Model No. MC14518CP includes two Binary Coded Decimal Up-Counters, each of which would be suitable for use in this invention as counter 32.

The output of binary coded decimal counter 32 is applied to line 37 which becomes the input line to a three-digit binary coded decimal counter 34. The three-digit binary coded decimal counter provides a three-decade count of the number of pulses applied to counter 34 at the clock terminal C. Counter 34 also comprises a multiplexer (not shown) and a scanning oscillator (not shown) which permit time division multiplexing of each of the three one-digit counters so that the output signals on terminals Q0 through Q3, respectively, are each sequenced so that in combination they represent either the first, second, or third decade at any one time. Digit select signals available at terminals $\overline{DS1}$, $\overline{DS2}$, and $\overline{DS3}$ are also sequenced by the scanning oscillator to synchronously activate the appropriate decimal indicator for the decade being generated by the three-digit counter 34. A Motorola MC14553CP three-digit BCD counter is an example of one such counter that would be suitable for use in this invention. Capacitor Cf, connected between terminals 3 and 4 of the three-digit binary coded decimal counter 34, determines the scan frequency used for time multiplexing the output of the counter 34. One thousand picofarads (1000pf) is an acceptable value of capacitor $C_f$ for purposes of this invention.

The output signals of the three-digit binary coded decimal counter 34 are applied to lines 39, 41, 43, and 45, respectively, on which they are transferred to decoder 36. Decoder 36 receives four-bit binary coded decimal signals and decodes such signals to drive seven-segment display indicators 40, 42, and 44. One such decoder that would be suitable for use in this invention is a Texas Instruments Model No. SN7447A BCD to Seven-Segment Decoder/Driver. The output signals of the decoder 36 are applied to a resistor network so that each of the seven output signals from the decoder unit are current limited by a resistor of suitable value. A Sprague type 914C-SR Resistor Network with a set of seven resistors of approximately 75 ohms each, is a suitable resistor network for use in this invention.

The output lines of resistor network 38 are applied to three decimal indicators 40, 42, and 44, respectively. Although there are many decimal indicator devices available that would be suitable for use in this invention for the purpose indicated, the preferred embodiment of this invention employs three common anode LED displays, each having about a 0.3 inch high character. The Hewlett Packard Model No. 5082-7730 Solid State Seven-Segment Indicator is an example of a suitable decimal indicator for use in this invention.

Each of the indicators 40, 42, and 44 has a single anode which is connected to +5 volts DC by means of transistor switches 46, 48, and 50, respectively. Only one switch is closed at any one time in accordance with the digit select signals generated by the three-digit binary coded counter 34 at terminals DS1, DS2, and DS3. If the scanning oscillator frequency in the three-digit binary coded decimal counter 34 is high enough, say greater than 100 cycles per second, because of persistence of vision, there is no apparent flicker and the decimal indicators appear to be continuously illuminated.

It will now be apparent to those skilled in the electronics art that the three-digit binary coded counter 34 may be replaced by three or more discrete counters and also that circuit means may be provided for indicating an overflow condition or for stopping the count when an ususually high particle count exceeds the highest number that can be displayed.

Thus, it is seen that platelet pulse counter 24 and platelet pulse count display system 26, together comprise a counting and display system that produces a count of the platelet pulses applied from the pulse sorting unit 22 and then displays the three most significant digits of that count which, as will be seen shortly, are the number of thousands of platelets per microliter of the blood sample being tested. As the platelet pulse count progresses, the displayed digits continue to change in accordance with the output signals of the three-digit binary coded decimal counter. In most cases, the platelet count display would be changing slowly enough to allow visual observation during the counting process. The rhythm established by that counting is a useful indication of the uniformity of the sample flow through the transducer.

When the counting process is completed, the final platelet count is displayed until the power is removed or the counters are reset, as explained below.

Red blood cell pulses are transferred from pulse sorting unit 22 or 181 to red blood cell pulse counter 28 over line 33 and are applied to binary coded decimal counter 52. Counter 52 may be the same type of counter as binary coded decimal counter 32 used in platelet pulse counter 24. The input pulses are applied to terminal E, that is, the enable terminal of the counter 52 and the output signal is available at terminal Q4. The output signal of counter 52 is a pulse generated once for every ten input pulses counted. The output signal of binary coded decimal counter 52 is applied to line 53 which is connected to the enable terminal E of binary coded decimal counter 54. Counter 54 may be the same type of counter as binary coded decimal counter 52. The output signal of binary coded decimal counter 54, available at terminal Q4, is a pulse generated once for each ten input pulses counted. Therefore, for each 100 red blood cell pulses generated by logic sorting unit 22, counter 54 generates one pulse. Thus, binary coded decimal counter 52 and binary coded decimal counter 54 together comprise a fixed two-decade prescaler or divider 51. An alternative prescaler circuit that provides a certain degree of adjustability and that may be substituted directly for the prescaler circuit 51, is indicated in FIG. 4 and is discussed in detail below in conjunction with FIG. 4.

At this point it will be recalled that the objective in counting red blood cells along with platelets, is to reach a count of the number of red blood cells that corresponds to the previously known or assumed red blood cell density of the blood sample being tested. When the blood cell count reaches a number that corresponds to the previously known or assumed density, it is desirable to stop the counting processes taking place in both counters, red blood cell pulse counter 28, and platelet pulse counter 24, so that the number of platelets displayed at that time corresponds to the platelet density of the blood sample being tested.

As previously noted, stopping only the platelet pulse counting process when the red blood cell pulse counter attains the preset count and merely registering the platelet count when that equality is attained, without stopping either counting process, are each encompassed within the scope of this invention.

Prior to commencement of the counting operation, the three most significant digits of the previously known red blood cell count density are set into, that is registered and held by binary coded decimal thumbwheel switches 65, 75, and 85, respectively, that together comprise thumbwheel switch array 30. During the counting operation, the output signal of binary coded decimal counter 54 is applied to the series combination of the three binary coded decimal counters 56, 66, and 76, respectively. These three counters are connected in series so that each develops a count corresponding to one decade of the three most significant digits of the red blood cell count.

Binary coded decimal counters 56, 66, and 76 may each be the same type of counter as binary coded decimal counter 52. Each thumbwheel switch of thumbwheel switch array 30 may, by way of example, be a Digitran Model No. 28015 binary coded decimal thumbwheel switch. Each binary coded decimal counter 56, 66, and 76 produces four output signals on its output terminals Q1, Q2, Q3, and Q4, respectively, corresponding to the 1, 2, 4, and 8 binary digit column of the corresponding decade. Each such output signal is applied through a diode to the appropriate binary column terminal (i.e., 1, 2, 4, or 8) of thumbwheel switches 65, 75, and 85, respectively. The output signals at terminal Q4 of binary coded decimal counter 56 are applied to the enable terminal E of binary coded decimal counter 66 and the output signals at terminal Q4 of binary coded decimal counter 66 are applied to the enable terminal E of binary coded decimal counter 76. As a result, binary coded decimal counter 56 will produce one pulse at its terminal Q4 for each thousand red blood cell pulses counted, and binary coded decimal counter 66 will produce one pulse at its terminal Q4 for each ten thousand red blood cell pulses counted. Therefore, the actual count corresponding, for example, to the digits 488 shown displayed in the thumbwheel switch array 30 in FIG. 1, is 48,800 red blood cells. A red blood cell count of 48,800 actually corresponds to 0.01 µl of a blood sample containing 4.880 million red blood cells/µl.

As previously discussed in conjunction with FIG. 3, the red blood cell count is prescaled by a factor of 100 and the platelet count is prescaled by a factor of 10. Therefore, if thumbwheel switch array 30 has been set to display the number 488, the actual number of red blood cell pulses on red blood cell pulse line 33 corresponding to such a count, is 48,800. Thus, for a diluted sample having a red cell density of 48,800 per microliter, 1 microliter of diluted sample will have passed through the sensing zone of the transducer in order to yield such a count. Simultaneously therewith, the number of platelet pulses occurring on platelet pulse line 35 will be approximately 3040 during that same interval. Obviously, 3040 platelets in a volume of 1 microliter of whole blood diluted to 1/100 of its original concentration, corresponds to a platelet density of 304,000 platelets per microliter of undiluted whole blood. Therefore, prescaling the platelet pulse count by 10 yields a count display of 304 which is then displayed as a count of thousands of platelets per microliter of whole blood.

Each of the binary coded decimal counters 56, 66, and 76 produces approximately 0 volts DC at terminals Q1, Q2, Q3, and Q4 for a binary ZERO and each produces approximately +45 volts DC at each of those same terminals for a binary ONE. As long as the binary count produced by each of the binary coded decimal counters 56, 66, or 76 is less than the decimal count set into the corresponding thumbwheel switches 65, 75, and 85, respectively, common line 90 remains electrically connected to ground potential through at least one of the diodes 58, 60, 62, 64, 68, 70, 72, 74, 78, 80, 82, and 84. However, when the binary count generated by each of the binary coded decimal counters 56, 66, and 76 becomes equal to the setting of the corresponding thumbwheel switch 65, 75, and 85, respectively, none of the twelve possible paths through the appropriate diodes is connected to ground potential G. At that time, no current flows through pullup resistor $R_p$ and the voltage on line 90 increases to +5 volts DC, producing a TRUE count terminating signal STOP.

As shown in FIG. 3, count terminating signal STOP is applied to the clock terminal C of binary coded decimal counter 52 in red blood cell pulse counter 28 and to the clock terminal C of binary coded decimal counter 32 in platelet pulse counter 24. A TRUE count terminating signal STOP inhibits any further changes in those two binary coded decimal counters and therefore both counting processes are immediately terminated.

A reset line R/S is available to reset all binary coded decimal counters prior to starting a new test. When the reset line is connected to a +5 volt source, all of the counters are reset to a count of zero, making them ready for a new test. Reset line R/S may be connected to such a source by means of a conveniently located momentary spring-loaded switch (not shown) making it convenient for an operator to reset the counters at an appropriate time.

As previously indicated, the fixed prescaler 51 shown in FIG. 3, may be replaced by a prescaler that provides some degree of adjustability. Such an adjustable prescaler 251 is shown generally in FIG. 4. Replacement of fixed prescaler 51 with adjustable prescaler 251 permits division of the red blood cell count by any integer within the range 100 to 109 inclusive.

Division by an integer other than 100 in the red blood cell counter may sometimes be desirable to bias the count of red blood cells whereby the resultant platelet densities are higher and thus more closely correlated with platelet counters of other types that would ordinarily indicate such higher densities.

Details of the adjustable prescaler will now be described in conjunction with FIG. 4. As indicated in FIG. 4, adjustable prescaler 251 includes two binary coded decimal counters 252 and 254 which may be identical in all respects to the binary coded decimal counters 52 and 54 of fixed prescaler 51 of FIG. 3. The red blood cell pulse line 33 is applied to the enable terminal E of BCD counter 252. BCD counter 252 generates a pulse at its output terminal Q4 for each tenth pulse applied to its enable terminal E. Connecting line 253 transfers the output pulses of BCD counter 252 to the enable terminal E of BCD counter 254. BCD counter 254 produces a pulse at its output terminal Q4 for each tenth input pulse applied to its enable terminal E. Thus, BCD counters 252 and 254 operate precisely the same as the two counters 52 and 54 in fixed prescaler 51 of FIG. 3. However, unlike the prescaler 51 of FIG. 3, the output signal of BCD counter 254 available at output terminal Q4 is not applied to line 55 until additional pulses, equal in number to the switch setting in thumbwheel switch 257, are received by the prescaler 251 on red blood cell pulse line 33.

The output signal at terminal Q4 of BCD counter 254 is applied to an inverter in the form of NOR-gate 260 by conductors 268, 269, and 270. The output signal of NOR-gate 260 is applied to the clock terminal CL of D-type flip-flop 258 by means of conductor 271. D-type flip-flop 258 may be, by way of example, one-half of a Motorola MC4013 dual D-type flip-flop circuit. As seen in FIG. 4, the data terminal D of flip-flop 258 is permanently tied to +5 volts DC. As a result, when the flip-flop is clocked by means of a pulse applied to its clock terminal CL, the output terminal Q of flip-flop 258 becomes positive, that is TRUE, and the output terminal $\overline{Q}$ becomes negative, that is FALSE. Flip-flop 258 output terminals Q and $\overline{Q}$ are tied respectively to the clock terminals CL of BCD counters 252 and 256. The positive signal applied to the clock terminal of the counter 252 inhibits further change in that counter and the negative signal applied to the clock terminal of the counter 256 enables that counter to commence the counting of pulses transferred to its input terminal E. Therefore, in effect, D-type flip-flop 258 is a decision gate that enables either BCD counter 252 or BCD counter 256 to count the red blood cell pulses transferred to the prescaler 251 on pulse line 33. It will now be apparent that this transfer in the enablement of the counting of the pulses on line 33 from BCD counter 252 to BCD counter 256 occurs when 100 pulses have been counted by BCD counter 252.

BCD counter 256 output terminals Q1, Q2, Q3, and Q4 are connected to thumbwheel switch 257 by means of diodes 263 through 266 respectively, in the same way that BCD counters 56, 66, and 76 are connected to their respective thumbwheel switches 65, 75, and 85 previously described in conjunction with FIG. 3.

The common terminal C of thumbwheel switch 257 remains at ground potential, that is, 0 volts DC, until BCD counter 256 reaches a count corresponding to the count set into thumbwheel switch 257. Since the common terminal C of thumbwheel switch 257 is connected by means of conductor 282 to the D terminal of D-type flip-flop 259, the state of the flip-flop 259 remains fixed with its output terminal Q at approximately 5 volts DC corresponding to a TRUE condition, and output Q at 0 volts DC corresponding to a FALSE condition. The clock terminal CL of D-type flip-flop 259 is connected by means of connection 275 to pulse line 33 and therefore flip-flop 259 is clocked each time a pulse is received on line 33.

The D terminal of D-type flip-flop 259 is also connected through a resistor 267 to the Q terminal of D-type flip-flop 258 by means of connection 273. Resistor 267 acts as a pull-up resistor, similar to resistor $R_p$ of FIG. 3. Terminal Q of flip-flop 258 acts as a 5 volt DC source to drive terminal D of flip-flop 258 to +5 volts DC when the common terminal of thumbwheel switch 257 is disconnected from ground potential. Common terminal C of thumbwheel switch 257 is disconnected from ground potential when the BCD counter 256 achieves a count equal to the count set in thumbwheel switch 257. In response thereto, the voltage at terminal D of flip-flop 259 rises to the voltage at terminal Q of flip-flop 258, namely, about +5 volts DC. As a result, the output terminals Q and $\overline{Q}$ of D-type flip-flop 259 will change state at the occurrence of the next red blood cell pulse received on line 33. At that time, output terminal Q of flip-flop 259 will become positive, that is, approximately +5 volts DC, and output terminal $\overline{Q}$ will become negative, that is, approximately 0 volts DC. Then the negative-going signal at output terminal $\overline{Q}$ of flip-flop 259 is applied to line 55 which, as shown in FIG. 3, would be connected to the enable terminal E of the times 100 BCD counter 56.

Thus, it can be seen that by means of adjustable prescaler 251, a pulse is applied to line 55 each time the number of pulses received on line 33 equals 100 plus the number set in thumbwheel switch 257.

The output terminal Q of D-type flip-flop 259 is connected to one input of NOR-gate 261 by means of conductor 277. The output of NOR-gate 261 is connected to both input terminals of NOR-gate 262 by means of conductor 278. The output of NOR-gate 262 is connected by means of connection 279, 280, and 281 to the reset terminals of BCD counter 256 and D-type flip-flop 258 respectively. Accordingly, when the signal on output terminal Q of D-type flip-flop 259 becomes positive, positive signals are also applied to the reset terminals of BCD counter 256 and D-type flip-flop 258 respectively. As a result, BCD counter 256 is reset to a count of 0 and flip-flop 258 is reset so that the signal on output terminal Q of flip-flop 258 becomes FALSE, that is, about 0 volts DC, and the signal on output terminal $\overline{Q}$ of flip-flop 258 becomes TRUE, that is, approximately 5 volts DC. Thus, as BCD counter 256 is reset to 0, it is also disabled by having the voltage at its clock terminal C set positively and BCD counter 252 is enabled by having the voltage at its clock terminal C set negatively whereby BCD counters 252 and 254 are ready to count the next 100 pulses being received on pulse line 33.

To illustrate the operation of adjustable prescaler 251, it will be assumed for purposes of discussion, that thumbwheel switch 257 is set to the number 5 whereby a negative-going pulse will be applied to line 55 for each 105 pulses received on line 33. While the first 100 pulses are being received, BCD counters 252 and 254 are enabled and BCD counter 256 is disabled. When the 100th pulse is received on line 33, BCD counter 254 produces a positive output signal at its terminal Q4. In response thereto, D-type flip-flop 258 is clocked, setting its output terminal Q positive, its output terminal $\overline{Q}$ negative, and causing the disabling of BCD counter 252 and the enabling of BCD counter 256. BCD counter 256 then takes over the counting and proceeds to count in accordance with further pulses received on line 33. When the 105th pulse is received on line 33, that will be the fifth pulse received by BCD counter 256 during its enabled condition, and thus BCD counter 256 will produce an output on its terminals Q1 through Q4 respectively, corresponding to a count of 5, the same count preset in thumbwheel switch 257. As a result, thumbwheel switch common terminal C will be disconnected from ground potential, that is, 0 volts DC, allowing the data terminal D of D-type flip-flop 259 to reach the potential of the output terminal Q of flip-flop 258, namely, about 5 volts DC. Thereafter, upon receipt of a clock pulse by flip-flop 259, terminal $\overline{Q}$ of flip-flop 259 applies a negative-going signal to line 55, and that signal is counted by the first of the BCD red blood cell counters 56 (see FIG. 3).

It will be observed that if it is desirable to divide by 100 as presently provided in the fixed prescaler 51 of FIG. 3, thumbwheel switch 257 of adjustable prescaler 251 is set to 0 whereby the 0 state of BCD counter 256 immediately upon its being enabled, allows the data terminal of flip-flop 259 to reach the +5 volt DC potential of the output terminal Q of flip-flop 258.

The reset signal on reset line R/S, and the count terminating signal STOP on line 90, serve the same functions previously described in conjunction with FIG. 3.

COINCIDENCE EFFECTS AND OTHER SOURCES OF ERROR

It will be understood that if the rate of flow of cells through the particle transducer is very small, either very few cells will be counted, or else a long time will be required to complete the test. In either event if the total count is small, statistical sampling errors will occur because the cells are not uniformly spaced along the axis of the flow path. On the other hand, if the particle density is very high, some of the particles will flow through the transducer in close proximity to each other thereby producing pulses that overlap. In this invention, the total count for each type of cell is made high enough to avoid significant statistical errors at the low range, and the flow rate is set at a value below that corresponding to maximum interference between pulses due to proximity effects. Furthermore, in this invention, pulses having amplitudes in different ranges are counted and the ratio of the counts is determined in order to substantially reduce errors that might otherwise arise because of such interference.

Since the proportions of error in both counts are nearly equal when two types of particles are being counted, the errors in the count of one type of particle is compensated for by errors in the count of the other type of particle. In this invention, such compensation is achieved by ascertaining the ratio of counts in equal times or more simply by employing the occurrence of a predetermined count of one particle to automatically determine the period over which the other type of particle is counted. In either event, knowledge of the concentration of one type of particle, e.g., red blood cells, aids in determining the concentration of another type of particle, e.g., platelets. It will be understood that the values of the concentration may be expressed in terms of particles per microliter or in terms of hematocrit, that is, volumetric fractions.

It will be understood that, because of interference due to coincidence, the number of pulses detected is less than the number of particles that flow through the transducer. The difference in the number of particles that have flowed through the transducer and the number of pulses that are counted, is sometimes referred to as a coincidence loss.

It can be shown that the rate at which pulses are generated is given, to a close approximation, by the following formula $$n = N(1 - CN)$$

where $n$ = number of pulses generated per second
$N$ = number of cells flowing through the transducer per second
$C$ = a coincidence loss factor the "coincidence losses" in unit time is given by the product $CN^2$.

The total number of cells detected in a time interval T is then $nT$. The statistical error, that is, the difference in counts detected in a short time interval T compared with a long time, can be reduced by increasing T.

It can be shown that, in general the count rate has a maximum theoretical value $$n = (1/4C)$$

For a particle transducer having a length of 78μ and a diameter of 55μ, it was determined from a series of experiments that the value of the coincidence loss factor C was $$C = 43.6 \ \mu sec \text{ per red blood cell}$$

where the flow rate was such that the transit time of a cell through the jewel was 66 μsec.

A method for measuring the coincidence loss factor is described in CALIBRATION, COINCIDENCE CORRECTION, AND INTERPRETATION OF COULTER COUNTER DATA, *Proceedings of the 5th Coulter Counter User's Conference,* San Francisco, California, Oct. 21–22, 1965, by L. H. Princen and in IMPROVED DETERMINATION OF CALIBRATION AND COINCIDENCE CORRECTION CONSTANTS FOR COULTER COUNTERS, *Review of Scientific Instruments,* Vol. 37, No. 10, pp 1416–1418, Oct. 1966, by L. H. Princen.

The corresponding maximum theoretical count rate was calculated to be:

$$n_{max} = 5{,}733 \text{ RBC/sec}$$

When operating at a count rate of 3000 pulses/sec, just over half the theoretical maximum, the actual number of cells flowing through the jewel was 3500, representing a coincidence loss error of 14.3%.

As a first approximation, because the density of the platelets is small compared with the density of the red blood cells, the error due to coincidence of platelets flowing through the jewel concurrently with red blood cells, would be about the same, namely, 14%. By automatically counting the pulses due to the red blood cells electronically, and automatically counting the pulses due to the platelets electronically, and automatically cutting off the counting of the platelet pulses when the predetermined red blood cells count has been reached, in the manner set forth above, theoretically at least, the two errors fully compensate each other and the correct value of the platelet count is indicated. Substantially correct results with substantially full compensation for coincidence errors can be achieved even when the red blood cell density is so high that the red blood cell flow rate is as much as 11,000 particles per second. Actually, the results are not as good as they appear this way. More particularly, in the better form of the invention illustrated in FIGS. 2A and 2B, residual masking effects result from the fact that when a platelet flows through the transducer in near coincidence with a red blood cell, the pulse is more likely to be counted by the red blood cell counter. Actually, when the red blood cell count rate was 3000 RBC/second in this version of the invention, losses in the platelet count for over about 90% of a series of tests ranged between 3% and 7% from a variety of causes, including coincidence effects.

The reason for this is that red blood cells are counted more frequently when near-coincidence occurs because some platelet pulses are lost in the steep rising portion of the red blood cell pulse.

By taking the ratio of the two pulse rates, errors due to coincidence effects alone are substantially reduced if the pulse rate is between about 20% and about 75% of the maximum. In the best embodiment of the invention, the ratio is automatically calculated electronically. In those cases where systematic errors appear, the reading may be automatically corrected by setting the red blood cell pulse prescaler 251 (FIG. 4) at a suitable value so that the correct platelet count may be read directly from the instrument.

Under some circumstances all coincidences are read as one type of particle such as red blood cells. This would occur, for example, in the first form of the invention described above where precautions have not been taken to control the counting in accordance with the first of two pulses that overlap. In such a case, full advantages of the invention are not obtained. In contrast, advantages of the invention are achieved extensively where first-pulse detection and signal-hold features are utilized, as in the second embodiment of the invention.

In most cases the sizes of the red blood cells lie outside the range of the sizes of the platelets and vice versa. However, there are cases in which the range of sizes of red blood cells and the range of sizes of platelets overlap at least to some extent. Generally speaking, it is well known that few platelets have sizes greater than 27.5μ$^3$ and that very few red blood cells have a size less than 27.5μ$^3$. Accordingly, it has become common to measure the concentration of cells 27.5μ$^3$ or larger and to treat them as if they were red blood cells even though a few of them may be platelets and a number of them are white blood cells. For this reason, the threshold of the upper threshold detector 16 may be set at a voltage corresponding to a size of a 27.5μ$^3$ blood cell to utilize the pulses generated by particles that size and larger for operating the red blood cell pulse counter. It is interesting to note in this case that even though particles other than red blood cells are counted the pulse counter 28 produces a signal corresponding to the original volume of the blood sample.

It will be noted that where the "red blood cell" count has been derived from a machine such as the Coulter S machine, where all particles having a volume more than the critical size are counted, this count corresponds to a particular known volume of blood. Accordingly, when the apparatus of this invention is likewise set to count all such particles, the pulse counter 28 correctly indicates when the same volume of blood has been passed through the particle sensing transducer 10. Accordingly, the corresponding indication produced by the platelet pulse counter 24 indicates the number of platelets having a size less than $27.5\mu^3$ in that same volume. In this connection, therefore, it is to be noted that the density of platelets is correctly determined except for the slight error that arises from the fact that a small proportion of platelets has a volume greater than the critical amount.

VARIATIONS OF THE INVENTION

It will be understood from the foregoing description of the invention, that the threshold voltage corresponds to a particular size of particle when a blood sample flows through a particular transducer. Thus, the potentiometers may be set at various positions to produce pulses corresponding to cells in two predetermined size ranges.

When making use of a red blood cell count that has been measured with some other machine, it is desirable to set the threshold at such a point that the red-blood-cell count that is produced in the apparatus of this invention, corresponds to the count produced in such other machine. This applies even if the other machine has erroneously counted some particles other than red blood cells and has treated them as if they too were red blood cells. Such errors occur in virtually all the so-called red blood cell counting instruments now on the market, which count all cells having a volume above about $27.5\mu^3$. Thus, in such machines, white blood cells are counted as red blood cells since they are even larger than the red blood cells, and the count also includes some of the larger platelets. In counting platelets with the present invention, the threshold that separates the red blood cell pulses from the platelet pulses is usually set at a value that corresponds to about $27.5\mu^3$. Resulting errors in the platelet density are small.

We have found that there is a significant number of blood specimens that have platelet distributions in which a fair number of platelets have sizes above $30\mu^3$. For this and other reasons it is desirable to provide an arrangement in which the lower threshold that is employed for counting red blood cells is below the upper threshold at which pulses that are counted are attributed to platelets. Two simple circuits for achieving this result are illustrated in FIGS. 6 and 7, respectively.

Figure 6:
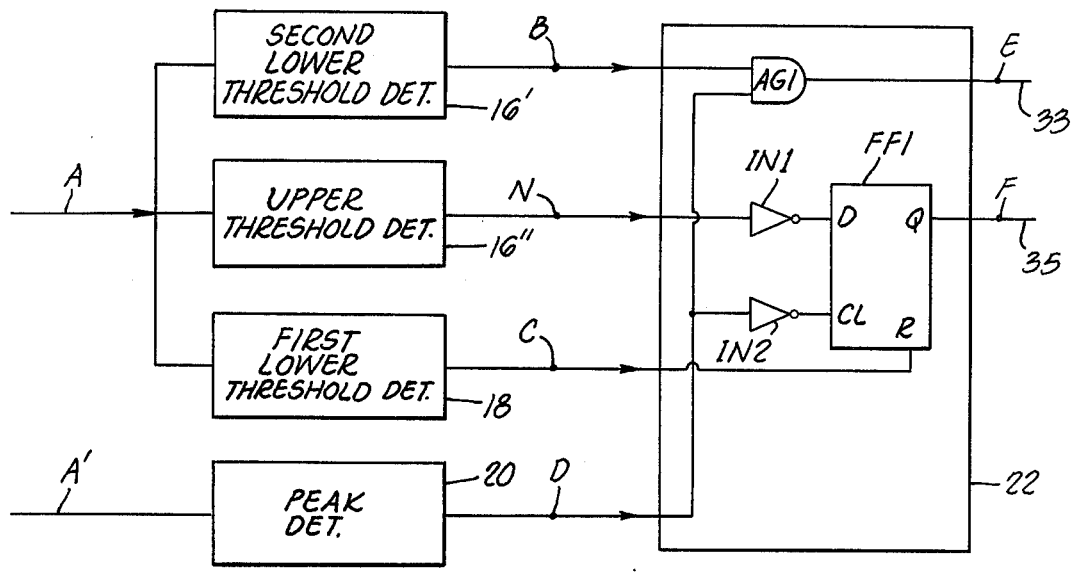
FIGS. 6 and 7 are schematic block diagrams of respective parts of two other embodiments of the invention.
Figure 7:
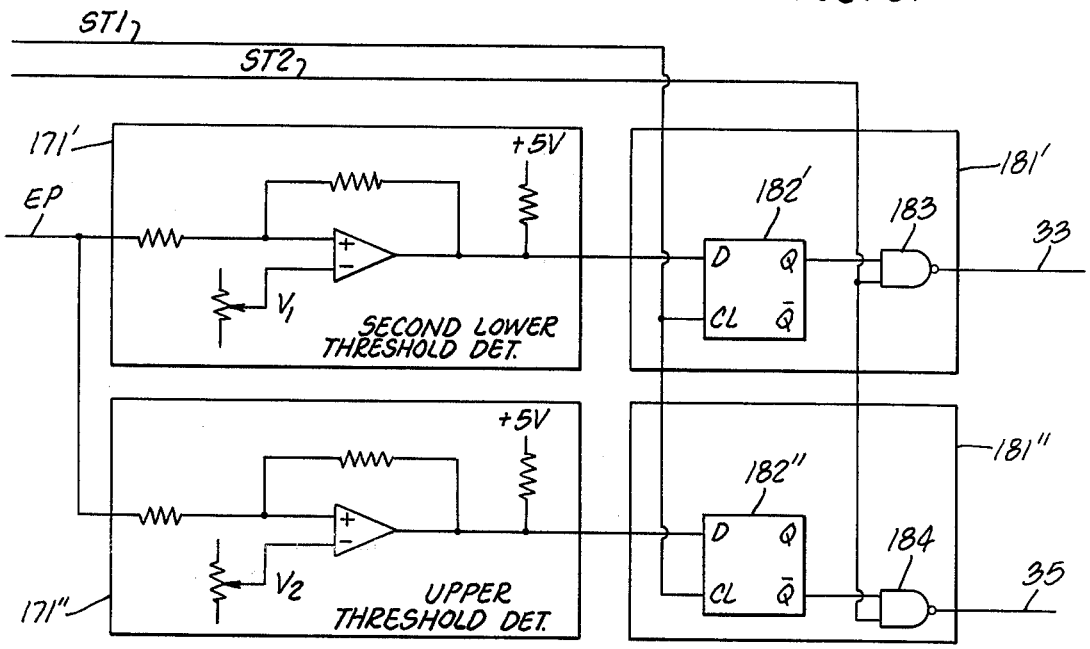

In the arrangement of FIG. 6, the upper threshold detector 16 of FIG. 1 is replaced by two threshold detectors 16' and 16". In this arrangement the threshold detector 18 is referred to as the first lower threshold detector. Threshold detector 16" is referred to as the upper threshold detector since it determines the upper threshold detection level for pulses which are counted as platelets. Threshold detector 16', on the other hand, is referred to as the second lower threshold detector since it determines the lower threshold detection level for pulses which are counted as red blood cells. The output of the lower threshold detector 16' is connected to the AND gate AG1 and the output of the upper threshold detector 16" is connected to the terminal D of flip-flop FF1 through the inverter IN1. The two threshold detectors 16' and 16" may be set at different levels with either above the other.

With this arrangement, the second lower threshold detector 16' establishes the minimum cutoff point for pulses that are treated as representative of red blood cells. Pulses having amplitudes above the threshold determined by the second lower threshold detector 16' produce red blood cell signals on line 33. A maximum cutoff point for red blood cells is a function of circuit element limitations.

With the arrangement of FIG. 6, pulses appearing at circuit point N inhibit the flip-flop FF1 if the detected pulse has an amplitude above the threshold for which the upper threshold detector 16" is set. Consequently, if a pulse has an amplitude in the range between a lower level established by the first lower threshold detector 18 and the upper threshold detector 16", a pulse appears on the line 35 but not otherwise.

It will be noted that in the arrangement of FIG. 6 if the threshold established in the detector 16" is above the threshold set for second lower threshold detector 16', pulses may appear on both lines 33 and 35 so that each pulse in that range is counted as both a red blood cell and as a platelet, even though, of course, the pulse normally represents only one such particle. This mode of operation is particularly useful when the machine that was originally used for counting red blood cells of the sample erroneously counted large platelets as if they were red blood cells. As more fully described below the second lower threshold detector 16' is set at a point that makes it possible to produce a number of pulses on line 33 corresponding to the red blood cell count that was made, even though it be erroneous, while the number of pulses produced on line 35 corresponds to the density of platelets in the sample. More particularly with this arrangement pulses are produced on line 33 corresponding to those produced in the machine that has erroneously counted such large platelets as red blood cells.

On the other hand, if the threshold established for the second lower detector 16' is above the threshold set in upper threshold detector 16", a situation may occur in which no pulse is produced on either line 33 or 35. Consequently, pulses that lie within the gap between the upper limit of the platelet pulse amplitude range and the lower limit of the red blood cell pulse amplitude range, are not counted at all.

By way of example, the platelet threshold detecting circuits 18 and 16" may be set at voltages corresponding to particles having volumes of $2.0\mu^3$ to $30.0\mu^3$ to detect platelets, while the second lower threshold above which particles are detected by the detector 16', may be set at a voltage corresponding to particles having a volume of $27.5\mu^3$ to detect red blood cells and large platelets that have been erroneously counted as red blood cells in the machine referred to above. In either case, the counting units 24, 28, and associated circuitry are operated as before to display a count in the platelet pulse counter 24 that is representative of the platelet density, though it only approximates that density.

The arrangement of FIG. 7 is similar to that represented in FIG. 2B. In this case, the upper threshold detector 171 of FIG. 2B is replaced by two threshold detectors 171' and 171", identical with the threshold detectors 16' and 16" of FIG. 6, and the pulse sorting unit 181 of FIG. 2B is replaced by two pulse sorting units 181' and 181". In this case, the flip-flop 182 of FIG. 2B is replaced by two flip-flops 182' and 182" respectively. One leg of the AND gate 183 is connected to the output terminal $\overline{Q}$ of flip-flop 182' and one leg of th AND gate 184 is connected to the output terminal Q of flip-flop 182". The remaining input legs of the two AND gates 183 and 184 respectively are connected to receive the strobe signal ST2. The data terminal D of flip-flop 182' is connected to the output of the second lower threshold detector 171' and the data terminal D of flip-flop 182" is connected to the output terminal of upper threshold detector 171". In this case, also, as in the case of FIG. 6, a pulse is produced on line 33 to be counted as a red blood cell pulse if the height of the detected pulse exceeds the threshold determined by the second lower threshold detector 171' and as a platelet if the pulse height lies in the range established by the lower threshold detector 111 (shown in FIG. 2A) and the upper threshold detector 171". In this case, as in the case of FIG. 6, the same pulse may be counted as a red blood cell pulse and as a platelet pulse if the two ranges overlap. Similarly, pulses that have amplitudes in a gap that may exist between the two ranges, are not counted at all.

A typical threshold setting for the upper threshold level, that is, the upper limit for detecting platelets, corresponds to a voltage V2 of 3.0 volts in the upper threshold detector 171". A typical threshold setting for the second lower threshold level, that is, the lower limit for detecting red blood cells, corresponds to a voltage V1 of 2.75 volts in the second lower threshold detector 171'. The 3.0 volt setting corresponds to a volume of $30\mu^3$ and the 2.75 volt setting corresponds to a volume of $27.5\mu^3$.

CONCLUSION

It will now be understood that this invention utilizes electronic cell counting to simultaneously count red blood cells and platelets and automatically ascertains and displays the platelet density of a blood sample and that the counting is controlled in accordance with the red blood cell density previously measured or otherwise ascertained.

It will also be understood that in this invention the platelet density of a diluted blood sample is determined, that is, representative of the test subject's total blood supply, even though no measurement is made of the volume of the sample. In fact, the accuracy of the measurement of platelet density by this invention does not depend upon knowledge of the precise volume being measured and does not depend upon the accuracy of the dilution from which the sample is prepared.

In addition, it will be understood that what is disclosed herein are a number of embodiments, including a preferred embodiment of an apparatus designed specifically to carry out the aforementioned method. This apparatus may utilize any one of many well-known particle sensing transducers that generate electrical signals, the amplitudes of which depend upon the size of the particles being sensed. This apparatus provides means for discriminating between electrical signals generated as a result of detection of platelets and electrical signals generated as a result of detection of red blood cells, to produce corresponding pulses on separate lines, one line being dedicated to counting red blood cells and one to counting platelets.

Furthermore, it will be understood that the apparatus of this invention includes counting means for separately counting such pulses until the number of red blood cells counted equals a preset value, and it also includes a count terminating signal generating means to automatically terminate the counting process at which time the displayed platelet pulse count corresponds directly to the platelet density of the sample under test without further manual (or mental) calculation.

Although in describing this invention reference has been made to specific illustrative embodiments thereof, many changes and modifications will become apparent to those skilled in the art without departing from the spirit and scope of the invention. For example, it will now be apparent, as a result of the teaching herein, that the method of this invention may be performed using apparatus other than the particular embodiment disclosed, namely, particle sorting devices capable of producing separate simultaneous counts and capable of being stopped by manual means. By way of further example, it will now also be apparent that this invention can be practiced in conjunction with a multichannel analyzer of the type that includes capabilities of pulse-height analysis, pulse count, and count display, such as the Model ND100 Multichannel Analyzer manufactured by Nuclear Data, Inc. of Schaumberg, Illinois.

A 1974 brochure describing the Nuclear Data ND100 Multichannel Analyzer, and a 1975 instruction book for operation of the controls of the ND100 Multichannel Analyzer and entitled "IM88-0551-00, Operator's Instruction Manual", have been published by Nuclear Data, Inc. and are expressly incorporated herein by reference. These two publications would make it apparent to one of ordinary skill in the art, having the teaching of Applicant before him, how to practice the invention herein disclosed in conjunction with the ND100 Multichannel Analyzer.

The use of the particular multichannel analyzer mentioned above, is not as satisfactory as the apparatus described in detail hereinabove because the multichannel analyzer does not include means for stopping the counting process when the red blood cell count corresponds to numbers other than to the particular count numbers for which the instrument has been calibrated. Thus, for example, if it is desirable to stop the counting process at a point corresponding to 4.88 million red blood cells per microliter, the nearest stopping point available on this particular instrument is 5.00 million red blood cells per microliter. Thus, when using such an instrument, if precision of counting is desired, an arithmetic correction must still be made. However, this instrument can be employed with facility where the counting interval is measured in terms of time.

It will now be apparent in view of the above description, that the Applicant's invention resides primarily in a method and apparatus for determining the count per unit volume, that is, the density or concentration, of particles in a sample of liquid of undetermined volume, and that there are numerous variations of elements of the apparatus and steps of the method that come within the scope of the invention, the invention not being limited to the particular embodiment disclosed herein.

It will also be apparent that circuits of the type already described for sensing, discriminating, sorting, and for use in counting, can be modified to be responsive to an electrical signal that is produced in the same apparatus as a manifestation of a reference particle concentration and that is applied to the counting apparatus, thereby precluding the need for manual setting of a reference concentration.

Additional variations in steps, or elements, or both, of the invention herein described, include the step of and means for determining the particle density or concentration of a plurality of different types of particles of unknown density or concentration. Another variation utilizes the additional step and means for adding a synthetic or non-synthetic particle of known concentration and volume, to a known volume of the sample fluid to synthetically produce an appropriate concentration of reference particles that may be used to determine the relative concentration of particles under test.

It is therefore to be understood that it is intended to include all changes and modifications as may reasonably and properly be included within the scope of the appended claims.

As discussed in the introductory portion of the present specification the broad concepts of the invention may be applied to density or concentration measured and expressed in other ways than count per unit volume; specifically for hematocrit in percent volume. In many laboratories the hematocrit of blood samples is established by a well-known centrifuging process. Thus many times hematocrit is more conveniently available as a characteristic of a specific sample of blood rather than the red blood cell count per unit volume. In other words, it may be more convenient to input hematocrit data by means of thumbwheel 30, as illustrated in FIG. 1, into the apparatus of the present invention rather than red blood cell count.

FIG. 8 illustrates the minor change in circuitry to accomplish this. The transducer 10 and ac amplifier 12 are the same as illustrated in FIG. 1 and the output A' or BLRI of ac amplifier 12 is inputed to a base line restorer 101 as illustrated in FIG. 2A. The restore output is BLRO as explained above which is connected to the peak hold circuit 131 also shown in FIG. 2A to produce the signal $E_p$.

As illustrated in FIG. 5, $E_p$ is a signal whose magnitude indicates either a platelet peak or a red blood cell peak. In accordance with the present modification of the invention rather than coupling $E_p$ to the circuitry of FIG. 2B, a hematocrit pulse converter unit 201 is provided which receives the $E_p$ waveform and converts it to a pulse train on its output line 33' which increments pulse counter 28 (see FIG. 1). Of course, the pulse counter is counting hematocrit pulses rather than RBC pulses. Thumbwheel switch 30' would contain the known hematocrit data of the blood sample being tested and in accordance with the invention when pulse counter 28 reaches the value of the thumbwheel switches 30' a stop signal generated also stops the platelet counter 24. Digital readout 26 then provides a platelet counter per unit volume.

Thus in summary the only major change in the existing circuitry is the use of a hematocrit pulse converter 201 which in effect integrates blood cell pulses represented by $E_p$ to provide the percent volume units necessary for the known standard hematocrit data. In order to provide proper timing ST 1 from unit 121 of FIG. 2A is used by the pulse converter along with a signal indicating that a red blood cell is present rather than the platelet (since $E_p$ may represent either) which is obtained from FIG. 6, line B or pin 4 of unit 172 of FIG. 2B.

Therefore, by a simple set of switches (not shown) the present apparatus can be converted from red blood cell count (number of particles per unit volume) to hematocrit (percent). Such switch is conveniently linked to thumbwheels 30.

FIG. 9 illustrates the unit 201 of FIG. 8 in more detailed schematic form. The signal $E_p$ is connected to the noninverting input of an operational amplifier 202 which is enabled at its negative inverting input by an output from a NAND gate 203. Such output occurs only at the coincidence of the timing pulse ST 1 (see FIG. 5) and the RBC present signal. The width of the $E_p$ portion selected is determined of course by ST 1 and may be approximately 5 microseconds for example.

The output of amplifier 202 drives a variable current source consisting of transistor 203 and resistor R. The collector of the transistor is connected to a storage capacitor C. The charge or current produced by this current source is $E_p$ divided by R and is designated $I_A$. The level of charge in capacitor C is monitored by a comparator 204 having a reference input. When the level exceeds the reference input, D-type flip-flop 205 is activated to produce an output on $\overline{Q}$ to a NOR gate 206. The other input of NOR gate 206 is controlled by the output of NAND gate 203 which thus controls the output of NOR gate 206. Normally this output clamps the constant current source $I_D$ through diode 207. However, when the current source is unclamped for the timing period of ST 1 it serves as a charge dispensing means so that $I_D$ discharges capacitor C to bring it back toward a level corresponding to the reference of comparator 204.

Thus, the circuit of FIG. 9 serves as an integrator for the peaks of the red blood cell pulses which indicate hematocrit. More importantly from an operational point of view common timing means control both the analog input voltage means 202 and the charge dispensing current $I_D$ so that they are only enabled during a common time interval of fixed duration. This greatly improves the accuracy of the circuit.

From an operational standpoint the amount of charge stored in C is $I_A$ (i.e., $E_p/R$) multiplied by T, the period of ST1. This is balanced by the digital charge pulse feedback circuit which produces $I_D \times T \times N_H$, where $N_H$ is the number of hematocrit pulses on line 33'. Thus the peaks of the RBC pulses are integrated (percent) and converted to a digital format.

In addition, by adjustment of circuit values the ratio of actual red blood cell pulses is perhaps 10:1 compared to a single hematocrit pulse produced on line 33'. In other words, several red blood cell pulses are required to charge capacitor C to a charge level so that the reference value of comparator 204 will be exceeded to cause production of a hematocrit pulse. Thus the largest peak value of $E_p$ will perhaps for example provide only a single hematocrit pulse. Such architecture greatly reduces errors in this type of conversion system.

The invention claimed is:

1. In apparatus for measuring the concentration of particles of a first type in a fluid in which first and second types of particles are suspended, the first and second types of particles generally differing in a detectable physical characteristic, in which apparatus particles suspended in such fluid are sensed as said fluid is flowed through sensing means, and electrical pulses corresponding to said sensed particles are generated, the pulses having an electrical characteristic that corresponds to said physical characteristic, the combination that comprises:
(a) means responsive to such electrical characteristics of said pulses for discriminating between types of particles in a specimen having different characteristics;
(b) means controlled by said discriminating means for generating separate signals corresponding to pulses generated by the particles in the specimen having the respective characteristics; and (c) a register and means for setting said register in accordance with the concentration of said second type of particle in said specimen and means controlled by the setting of said register as well as said separate signals for producing an output signal representative of the concentration of particles of said first type in said specimen.

2. In apparatus for measuring the concentration of particles of a first type in a fluid in which first and second types of particles are suspended, the first and second types of particles generally differing in a detectable physical characteristic, in which apparatus particles suspended in said fluid are sensed as said fluid is flowed through sensing means, and electrical pulses corresponding to said sensed particle are generated, the pulses having an electrical characteristic that corresponds to said physical characteristic, the combination that comprises:
(a) means responsive to such electrical characteristics of said pulses for discriminating between particles having different physical characteristics;
(b) means controlled by said discriminating means for generating two separate sets of signals corresponding to different proportions of said two types of particles;
(c) a register;
(d) means for setting said register in accordance with a standard concentration of said second type of particle when known; and
(e) means controlled by the set of said signals corresponding to the flow through said sensing means of a number of particles of said second type corresponding to said standard concentration and by said register for indicating the number of particles of said first type that has flowed concurrently through said sensing means.

3. In apparatus for measuring the concentration of particles of a first type in a fluid in which first and second types of particles are suspended, the first and second types of particles differing in a detectable physical characteristic, in which apparatus particles suspended in said fluid are sensed as a said fluid is flowed through sensing means and electrical pulses corresponding to said sensed particles are generated, the pulses having electrical characteristics that depend on the physical characteristics of said particles, and the pulses corresponding to particles of said first and second types having amplitudes that extend over corresponding different but overlapping first and second ranges respectively, the combination that comprises:
(a) first means for detecting pulses having an electrical characteristic in a first range corresponding primarily to particles of said first type;
(b) second means for detecting pulses having an electrical characteristic in a second range corresponding primarily to particles of said second type;
(c) means controlled by said first and second means for generating a first and a second stream of pulses respectively; and
(d) means controlled by said two streams of pulses to produce a signal representative of the ratio of concentrations of said two types of particles in said fluid including a register and means for setting said register in accordance with the concentration of said second type of particle, and means controlled by the setting of said register as well as said two streams of particles for indicating the concentration of said first type of particle in said fluid.

4. In apparatus for measuring the concentration of particles of a first type in a fluid in which first and second types of particles are suspended, the first and second types of particles generally differing in a detectable physical characteristic, in which particles suspended in said fluid are sensed as said fluid is flowed through sensing means, and electrical pulses corresponding to said sensed particles are generated, the pulses having an electrical characteristic that corresponds to said physical characteristic, the combination that comprises:
(a) means responsive to such electrical characteristics of said pulses for discriminating between particles differing in said physical characteristic;
(b) means controlled by said discriminating means for generating a first stream of pulses and a second stream of pulses corresponding to particles differing in said physical characteristics;
(c) means for registering a condition corresponding to the concentration of said second type of particle in said fluid;
(d) means controlled by said two streams of pulses and said registered condition for producing an output signal representative of the concentration of said first type of particle in said fluid; and
(e) display means for displaying said signal.

5. In apparatus for determining the particle density of a first type of particle suspended in a fluid in which a second type of particle is also suspended, wherein the first and second types of particles differ in a physical characteristic and wherein the particle density of the second type of particle is known, the improvement comprising:
a transducer adapted for detecting particles of the first and second types suspended in such a fluid and also adapted for generating an electrical signal corresponding to each detected particle, said signal being generally representative of whether said detected particle is a particle of the first type or of the second type;
a discriminator adapted for receiving said electrical signals and for separately generating a first electrical pulse for each received electrical signal generally representative of a particle of the first type and a second electrical pulse for each received electrical signal generally representative of a particle of the second type;
a first counter adapted for counting said first electrical pulses and for producing electrical count signals corresponding to said first count;
a second counter adapted for counting said second electrical pulses and for producing electrical count signals corresponding to said second count; and
means responsive to said count signals to stop counting by said first counter when said second count reaches a predetermined number corresponding to the known density of said second type of particle.

6. Apparatus for determining particle density as defined in claim 5, further comprising means for registering said first count in a visual display unit and means for displaying the value of said first count when said second count reaches said predetermined number.

7. An apparatus for determining the platelet density of a blood sample of undetermined volume the sample having a red blood cell density, the apparatus adapted for connection to a transducer adapted for detecting particles such as platelets and red blood cells in a blood sample, the transducer also adapted for generating an electrical signal corresponding to each detected particle, said signal being representative of where said detected particle is generally a platelet or is generally a red blood cell, the apparatus comprising:

discriminating means adapted for receiving said electrical signals and for separately generating a first electrical pulse for each received electrical signal generally representative of a platelet and a second electrical pulse for each received electrical signal generally representative of a red blood cell;
   first means for counting said first electrical pulses;
   second means for counting said second electrical pulses; and
   means for stopping said first counting means when said second counting means attains a predetermined count for determining said platelet density.

8. In apparatus for determining the platelet density of a blood sample of undetermined volume, the sample having a red blood cell density, which apparatus is adapted for connection to a transducer adapted for detecting platelets and red blood cells in a blood sample, said transducer also being adapted to generate an electrical signal in one range of amplitudes generally corresponding to each detected platelet and an electrical signal in another range of amplitudes generally corresponding to each detected red blood cell:

a discriminator adapted for receiving said electrical signals and for separately generating a first electrical pulse for each received electrical signal the amplitude of which is representative of a detected platelet and a second electrical pulse for each received electrical signal the amplitude of which is representative of a detected red blood cell;
   a first counter for counting said first electrical pulses;
   a second counter for counting said second electrical pulses; and
   means responsive to said second counter and controlling said first counter for stopping said first counter when the count produced by said second counter corresponds to said red blood cell density.

9. An apparatus for determining particle density as defined in claim 8, the discriminator comprising:
   a lower threshold detector for generating a first detection signal for each transducer-generated electrical signal having an amplitude that exceeds a lower threshold;
   an upper threshold detector for generating a second detection signal for each transducer-generated electrical signal having an amplitude that exceeds an upper threshold; and
   gate-circuit means adapted for receiving said first and second detection signals and also adapted for generating only said first electrical pulse when only said first detection signal is received, and for generating only said second electrical pulse when said first and second detection signals are received substantially simultaneously.

10. An apparatus for determining particle density as defined in claim 9, the discriminator further comprising:
   a peak detector for generating a third detection signal when each transducer-generated electrical signal reaches its peak amplitude;
   said gate-circuit means being also adapted for receiving said third detection signal and for generating said first or second electrical pulse only when receiving said third detection signal.

11. An apparatus for determining particle density as defined in claim 8, the discriminator further comprising means for detecting a peak level of each transducer-generated electrical signal and means for generating a peak-holding electrical signal corresponding to said each transducer-generated electrical signal, each said peak-holding electrical signal reaching and maintaining said peak level of said corresponding transducer-generated electrical signal.

12. An apparatus for determining particle density as defined in claim 11, said discriminator peak level detecting means comprising means responsive to only the first occurring peak of said transducer-generated electrical signal.

13. An apparatus for determining particle density as defined in claim 11, said discriminator further comprising means for resetting said peak-holding electrical signal generating means.

14. An apparatus for determining particle density as defined in claim 8, at least one of said counters comprising a prescaler device for dividing by a known factor, the number of electrical pulses counted.

15. An apparatus for determining particle density as defined in claim 14, said prescaler device comprising:
   settable integer means and logic circuit means responsive to the setting of said integer means whereby said known factor corresponds to said setting.

16. A method of ascertaining the particle density of a first type of particle suspended in a fluid in which a second type of particle is also suspended wherein the first and second types of particles generally differ in a physical characteristic, comprising the following steps:
   (a) measuring the particle density of said second type of particle;
   (b) flowing a sample of said fluid through a sensing zone;
   (c) sensing particles suspended in said fluid sample as said particles pass through said sensing zone;
   (d) generating electrical pulses corresponding to sensed particles, such pulses having different electrical characteristics that depend primarily upon differences in physical characteristics of the two types of particles;
   (e) electrically discriminating between pulses according to their electrical characteristics by separately detecting first and second pulses;
   (f) electrically separately counting first pulses and second pulses having different electrical characteristics to produce first and second counts; and
   (g) detecting said first count when said second count attains a value corresponding to the density of said second type of particle in said fluid.

17. In a method of ascertaining the particle density of a first type of particle suspended in a fluid in which a second type of particle is also suspended, wherein the first and second types of particles generally differ in a physical characteristic and wherein the particle density of the second type of particle is known; the steps:
   (a) flowing a sample of said fluid through a sensing zone;
   (b) sensing particles suspended in said fluid sample as said particles pass through said sensing zone;
   (c) generating electrical pulses corresponding to the particles sensed, each pulse having a different electrical characteristic that corresponds respectively to said different physical characteristics;

(d) utilizing said electrical characteristic of said each pulse to discriminate first pulses primarily generated by said sensing of said first type of particle from second pulses primarily generated by said sensing of said second type of particle;

(e) separately counting said first pulses and said second pulses to produce first and second counts respectively until said second count reaches a predetermined number that corresponds to said known particle density; and (f) developing an electrical signal representative of said first count when said second count equals said predetermined number.

18. In a method of ascertaining particle density as defined in claim 17, the step of stopping the counting of said first pulses when said second count equals said predetermined number.

19. A method of ascertaining particle density as defined in claim 17, further comprising the step of automatically displaying said first count referred to in step f).

20. A method of ascertaining the density of platelets suspended in a sample of blood of undetermined volume in which red blood cells are also suspended, wherein the density of the red blood cells is known; the method comprising the following steps:

(a) flowing such a sample of blood through a sensing zone;

(b) sensing platelets and red blood cells suspended in said blood sample as said sample flows through said sensing zone;

(c) generating an electrical pulse corresponding to each platelet and each red blood cell sensed, each pulse having an amplitude that corresponds, respectively, to the sizes of said platelets and said red blood cells, said amplitudes being separable by a threshold into a lower-amplitude group corresponding generally to platelets and into a higher-amplitude group corresponding generally to red blood cells;

(d) detecting whether the amplitude of said each pulse is above or below said threshold to discriminate first pulses generated primarily by said sensing of said platelets from second pulses generated primarily by said sensing of said red blood cells;

(e) separately counting said first pulses and said second pulses to produce first and second counts, respectively, until said second count reaches a predetermined number that corresponds to said known red blood cell density; and (f) automatically detecting and displaying said first count when said second count substantially equals said predetermined number whereby said noted first count corresponds to the density of said platelets.

21. In a method of ascertaining the particle density of a first type of particle suspended in a fluid in which a second type of particle is also suspended, wherein the first and second types of particles differ in a physical characteristic, the steps of:

(a) measuring the particle density of said second type of particle;

(b) flowing a sample of said fluid through a sensing zone;

(c) sensing particles suspended in said fluid sample as said particles flow through said sensing zone;

(d) generating an electrical pulse corresponding to each particle sensed, each pulse having a different electrical characteristic that corresponds, respectively, to said different physical characteristics;

(e) utilizing said electrical characteristics of said pulses to discriminate first pulses generally generated by said sensing of said first type of particle from second pulses generally generated by said sensing of said second type of particle;

(f) separately counting said first pulses and said second pulses to produce first and second counts, respectively, until said second count reaches a predetermined number that corresponds to said particle density of said second type of particle; and (g) automatically displaying said first count when said second count equals said predetermined number.

22. In a method of ascertaining particle density as defined in claim 21, comprising the step of stopping the counting of said first pulses when said second count equals said predetermined number.

23. A method of ascertaining particle density as defined in claim 21, comprising the step of stopping said counting of said first pulses and said counting of said second pulses when said second count equals said predetermined number.

24. In a method of ascertaining the particle density of platelets suspended in a sample of blood of undetermined volume in which red blood cells are also suspended, the steps:

(a) measuring the red blood cell density of such a sample;

(b) flowing said sample through a sensing zone;

(c) sensing each platelet and each red blood cell suspended in said sample as each platelet and red blood cell is flowed through said sensing zone;

(d) generating an electrical pulse corresponding to each platelet and red blood cell sensed, each said pulse having an amplitude that corresponds to the size of the particle sensed;

(e) utilizing said pulse amplitudes to discriminate first pulses generally generated by said sensing of said platelets from second pulses generally generated by said sensing of said red blood cells;

(f) separately counting said first pulses and said second pulses to produce first and second counts, respectively, until said second count reaches a predetermined number that corresponds to said density of said red blood cells; and (g) automatically displaying said first count when said second count equals said predetermined number whereby the density of said platelets is ascertained.

25. In apparatus for measuring the concentration of particles of a first type in a fluid in which first and second types of particles are suspended, the first and second types of particles generally differeing in a detectable physical characteristic, in which apparatus particles suspended in such fluid are sensed as said fluid is flowed through sensing means, and electrical pulses corresponding to said sensed particles are generated, the pulses having an electrical characteristic that corresponds to said physical characteristic, the combination that comprises:

(a) means responsive to such electrical characteristics of said pulses for discriminating between types of particles in a specimen having different characteristics;

(b) means controlled by said discriminating means for generating separate signals corresponding to pulses generated by the particles in the specimen having the respective characteristics; and (c) a register and means for setting said register in accordance with the concentration of said second type of particle in said specimen and means controlled by the setting of said register as well as said separate signals for producing an output signal representative of the concentration of particles of said first type in said specimen, said concentration of said second type of particle being in percent volume and including means for converting one of said separate signals to a digital format corresponding to such concentration such converter means comprising: charge storage means; analog input signal means responsive to said signal corresponding to said second type of particle for charging said charge storage means toward a level proportional to the magnitude of said signal; reference comparator means for comparing said level of charge in said storage means to a reference; charge dispensing means responsive to said comparator means to reduce said level of charge toward said reference; and common timing means for enabling said analog input signal means and said charge dispensing means during a common time interval of fixed duration and for producing a digital format signal corresponding to said concentration.

* * * * *